US007268222B1

(12) United States Patent
Harras et al.

(10) Patent No.: US 7,268,222 B1
(45) Date of Patent: Sep. 11, 2007

(54) POLYNUCLEOTIDES ENCODING HUMAN TRANSPORTER PROTEINS

(75) Inventors: Marie Harras, Spring, TX (US); Gregory Donoho, Portage, MI (US); C. Alexander Turner, Jr., The Woodlands, TX (US); Michael C. Nehls, Stockdorf (DE); Glenn Friedrich, Houston, TX (US); Brian Zambrowicz, The Woodlands, TX (US); Arthur T. Sands, The Woodlands, TX (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 1368 days.

(21) Appl. No.: 09/703,253

(22) Filed: Oct. 31, 2000

Related U.S. Application Data

(60) Provisional application No. 60/163,018, filed on Nov. 2, 1999.

(51) Int. Cl.
C07H 21/04 (2006.01)
C12N 15/00 (2006.01)
C12N 5/00 (2006.01)
C12N 1/20 (2006.01)
C12P 21/06 (2006.01)

(52) U.S. Cl. ............... 536/23.5; 435/69.1; 435/252.3; 435/320.1; 435/325; 435/471

(58) Field of Classification Search ............... 536/23.5; 435/69.1, 70.1, 71.1, 71.2, 252.3, 320.1, 435/325, 471; 530/300, 350
See application file for complete search history.

(56) References Cited

U.S. PATENT DOCUMENTS

| 4,215,051 | A |   | 7/1980  | Schroeder et al. |
| 4,376,110 | A |   | 3/1983  | David et al. |
| 4,946,778 | A |   | 8/1990  | Ladner et al. |
| 5,198,344 | A |   | 3/1993  | Croop et al. |
| 5,350,836 | A | * | 9/1994  | Kopchick et al. |
| 5,837,458 | A |   | 11/1998 | Minshull et al. |
| 5,866,699 | A |   | 2/1999  | Smyth |
| 5,869,336 | A |   | 2/1999  | Meyer et al. |
| 5,877,397 | A |   | 3/1999  | Lonberg et al. |
| 5,882,926 | A |   | 3/1999  | Amara et al. |
| 6,075,181 | A |   | 6/2000  | Kucherlapati et al. |

OTHER PUBLICATIONS

Vukicevic et al. PNAS USA 93:9021-9026, 1996.*
Massague J. Cell 49:437-8, 1987.*
Pilbeam et al. Bone 14:717-720, 1993.*
Skolnick et al. Trends in Biotech. 18:34-39, 2000.*
Bork P. Genome Research 10:398-400, 2000.*
Doerks et al. Trends in Genetics 14:248-250, 1998.*
Smith et al. Nature Biotechnology 15:1222-1223, 1997.*
Brenner SE. Trends in Genetics 15:132-133, 1999.*
Bork et al. Trends in Genetics 12:425-427, 1996.*
Suzuki, T., et al. Biochem. Biophys. Res. Comm. 238(3)790-794, 1997.*
Mahairas GG., et al. Proc. Natl. Acad. Sci. USA 96:9739-9744, 1999.*
Adams MD. Database GenEmbl. Accession No. B47956, Apr. 08, 1999.*
Tammur J., et al. Gene 273:89-96, 2001.*
Yabuuchi H., et al. Biochem. Biophys. Res. Commun. 288(4):933-939, 2001.*
Bird et al, 1988, "Single-Chain Antigen-Binding Proteins", Science 242:423-426.
Bitter et al, 1987, "Expression and Secretion Vectors for Yeast", Methods in Enzymology 153:516-544.
Colbere-Garapin et al, 1981, "A New Dominant Hybrid Selective Marker for Higher Eukaryotic Cells", J. Mol. Biol. 150:1-14.
Gautier et al, 1987, "α-DNA IV:α-anomeric and β-anomeric tetrathymidylates covalently linked to intercalating oxazolopyridocarbazole. Synthesis, physiochemical properties and poly (rA) binding", Nucleic Acids Research 15 (16):6625-6641.
Greenspan et al, 1993, "Idiotypes: structure and immunogenicity", FASEB Journal 7:437-444.
Huse et al, 1989, "Generation of a Large Combinatorial Library of the Immunoglobulin Repertoire in Phage Lambda", Science 246:1275-1281.
Huston et al, 1988, "Protein engineering of antibody binding sites: Recovery of specific activity in an anti-digoxin single-chain Fv analogue produced in *Escherichia coli*", Proc. Natl. Acad. Sci. USA 85:5879-5883.
Inoue et al, 1987, "Sequence-dependent hydrolysis of RNA using modified oligonucleotide splints and R Nase H", FEBS Letters 215(2):327-330.
Inoue et al, 1987, "Synthesis and hybridization studies on two complementary nona(2'-O-methyl)ribonucleotides", Nucleic Acids Research 15(15):6131-6149.
Inouye & Inouye, 1985, "Up-promoter mutations in the Ipp gene of *Escherichia coli*", Nucleic Acids Research 13(9):3101-3110.
Janknecht et al, 1991, "Rapid and efficient purification of native histidine-tagged protein expressed by recombinant vaccinia virus", PNAS USA 88:8972-8976.
Kohler & Milstein, 1975, "Continuous cultures of fused cells secreting antibody of predefined specificity", Nature 256:495-497.
Logan et al, 1984, "Adenovirus tripartite leader sequence enhances translation of mRNAs late after infection", Proc. Natl. Acad. Sci. USA 81:3655-3659.
Lowy et al, 1980, "Isolation of Transforming DNA: Cloning the Hamster aprt Gene", Cell 22:817-823.
Morrison et al, 1984, "Chimeric human antibody molecules: Mouse antigen-binding domains with human constant region domains", Proc. Natl. Acad. Sci. USA 81:6851-6855.
Mulligan & Berg, 1981, "Selection for animal cells that express the *Escherichia coli* gene coding for xanthine-guanine phosphoribosyltransferase", Proc. Natl. Acad. Sci. USA 78(4):2072-2076.

(Continued)

Primary Examiner—Robert S. Landsman
(74) Attorney, Agent, or Firm—Lexicon Pharmaceuticals, Inc.; Lance K. Ishimoto; Peter G. Seferian

(57) ABSTRACT

Novel human ATP binding cassette transporter polynucleotide and polypeptide sequences are disclosed that can be used in therapeutic, diagnostic, and pharmacogenomic applications.

4 Claims, No Drawings

OTHER PUBLICATIONS

Neuberger et al, 1984, "Recombinant antibodies possessing novel effector functions", Nature 312:604-608.

Nisonoff, 1991, "Idiotypes: Concepts and Applications", J. of Immunology 147:2429-2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527-1531.

Ruther et al, 1983, "Easy identificaton of cDNA clones", EMBO Journal 2(10):1791-1794.

Santerre et al, 1984, "Expression of prokaryotic genes for hygromycin B and G418 resistance as dominant-selection Markers in mouse L cells", Gene 30:147-156.

Sarin et al, 1988, "Inhibition of acquired immunodeficiency syndrome virus by oligodeoxynucleoside methylphosphonates", Proc. Natl. Acad. Sci. USA 85:7448-7451.

Smith et al, 1983, "Molecular Engineering of the *Autographa californica* Nuclear Polyhedrosis Virus Genome: Deletion Mutations within the Polyhedrin Gene", J. Virol. 46(2):584-593.

Stein et al, 1988, "Physiochemical properties of phosphorothioate oligodeoxynucleotides", Nucleic Acids Research 16(8):3209-3221.

Szybalska & Szybalski, 1962, "Genetics of Human Cell Lines, IV. DNA-Mediated Heritable Transformation of a Biochemical Trait", Proc. Natl. Acad. Sci. USA 48:2026-2034.

Takeda et al, 1985, "Construction of chimaeric processed immunoglobulin genes containing mouse variable and human constant region sequences", Nature 314:452-454.

Van Heeke et al, 1989, "Expression of Human Asparagine Synthetase in *Escherichia coli*", J. Biol. Chemistry 264(10):5503-5509.

Ward et al, 1989, "Binding activities of a repertoire of single immunoglobulin variable domains secreted from *Escherichia coil*", Nature 341:544-546.

Wigler et al, 1980, "Transformation of mammalian cells with an amplifiable dominant-acting gene", Proc. Natl. Acad. Sci. USA 77(6):3567-3570.

Wigler et al, 1977, "Transfer of Purified Herpes Virus Thymidine Kinase Gene to Bultured Mouse Cells", Cell 11:223-232.

Database EMBL [Online]ID: HSM801041, Sep. 15, 1999 Poustka et al.: "*Homo sapiens* mRNA" XP002163083.

\* cited by examiner

```
                        SEQUENCE LISTING

<160> NUMBER OF SEQ ID NOS: 25

<210> SEQ ID NO 1
<211> LENGTH: 1977
<212> TYPE: DNA
<213> ORGANISM: homo sapiens

<400> SEQUENCE: 1
atgacaagaa tggctgtgaa ggctcagcat cacacatctg aggtcagcga ccagcgcatc     60
cgtgtgacca gtgaagttct cacttgcatt aagctgatta aaatgtacac atgggagaaa    120
ccatttgcaa aaatcattga agacctaaga aggaaggaaa ggaagctatt ggagaagtgc    180
gggcttgtcc agagcctgac aagtataacc ttgttcatca tccccacagt ggccacagcg    240
gtctgggttc tcatccacac atccttaaag ctgaaactca cagcgtcaat ggccttcagc    300
atgctggcct ccttgaatct ccttcggctg tcagtgttct ttgtgcctat tgcagtcaaa    360
ggtctcacga attccaagtc tgcagtgatg aggttcaaga agtttttcct ccaggagagc    420
cctgttttct atgtccagac attacaagac cccagcaaag ctctggtctt tgaggaggcc    480
accttgtcat ggcaacagac ctgtcccggg atcgtcaatg gggcactgga gctggagagg    540
aacgggcatg cttctgaggg gatgaccagg cctagagatg ccctcgggcc agaggaagaa    600
gggaacagcc tgggcccaga gttgcacaag atcaacctgg tggtgtccaa ggggatgatg    660
ttaggggtct gcggcaacac ggggagtggt aagagcagcc tgttgtcagc catcctggag    720
gagatgcact tgctcgaggg ctcggtgggg gtgcagggaa gcctggccta tgtcccccag    780
caggcctgga tcgtcagcgg gaacatcagg gagaacatcc tcatgggagg cgcatatgac    840
aaggcccgat acctccaggt gctccactgc tgctccctga atcgggacct ggaacttctg    900
ccctttggag acatgacaga gattggagag cggggcctca acctctctgg ggggcagaaa    960
cagaggatca gcctggcccg cgccgtctat tccgaccgtc agatctacct gctggacgac   1020
cccctgtctg ctgtggacgc ccacgtgggg aagcacattt ttgaggagtg cattaagaag   1080
acactcaggg ggaagacggt cgtcctggtg acccaccagc tgcagtactt agaattttgt   1140
ggccagatca ttttgttgga aaatgggaaa atctgtgaaa atggaactca cagtgagtta   1200
atgcagaaaa aggggaaata tgcccaactt atccagaaga tgcacaagga agccacttcg   1260
gacatgttgc aggacacagc aaagatagca gagaagccaa aggtagaaag tcaggctctg   1320
gccacctccc tggaagagtc tctcaacgga aatgctgtgc cggagcatca gctcacacag   1380
gaggaggaga tggaagaagg ctccttgagt tggagggtct accaccacta catccaggca   1440
gctggaggtt acatggtctc ttgcataatt ttcttcttcg tggtgctgat cgtcttctta   1500
acgatcttca gcttctggtg gctgagctac tggttggagc agggctcggg gaccaatagc   1560
agccgagaga gcaatggaac catggcagac ctgggcaaca ttgcagacaa tcctcaactg   1620
tccttctacc agctggtgta cgggctcaac gccctgctcc tcatctgtgt gggggtctgc   1680
```

-continued

```
tcctcaggga ttttcaccaa ggtcacgagg aaggcatcca cggccctgca caacaagctc   1740
ttcaacaagg ttttccgctg ccccatgagt ttctttgaca ccatcccaat aggccggctt   1800
ttgaactgct tcgcagggga cttggaacag ctggaccagc tcttgcccat cttttcagag   1860
cagttcctgg tcctgtcctt aatggtgatc gccgtcctgt tgattgtcag tgtgctgtct   1920
ccatatatcc tgttaatggg agccataatc atggttattt gcttcattta ttatatg     1977
```

<210> SEQ ID NO 2
<211> LENGTH: 659
<212> TYPE: PRT
<213> ORGANISM: homo sapiens

<400> SEQUENCE: 2

```
Met Thr Arg Met Ala Val Lys Ala Gln His His Thr Ser Glu Val Ser
 1               5                  10                  15

Asp Gln Arg Ile Arg Val Thr Ser Glu Val Leu Thr Cys Ile Lys Leu
            20                  25                  30

Ile Lys Met Tyr Thr Trp Glu Lys Pro Phe Ala Lys Ile Ile Glu Asp
        35                  40                  45

Leu Arg Arg Lys Glu Arg Lys Leu Leu Glu Lys Cys Gly Leu Val Gln
    50                  55                  60

Ser Leu Thr Ser Ile Thr Leu Phe Ile Ile Pro Thr Val Ala Thr Ala
65                  70                  75                  80

Val Trp Val Leu Ile His Thr Ser Leu Lys Leu Lys Leu Thr Ala Ser
                85                  90                  95

Met Ala Phe Ser Met Leu Ala Ser Leu Asn Leu Leu Arg Leu Ser Val
            100                 105                 110

Phe Phe Val Pro Ile Ala Val Lys Gly Leu Thr Asn Ser Lys Ser Ala
        115                 120                 125

Val Met Arg Phe Lys Lys Phe Leu Gln Glu Ser Pro Val Phe Tyr
    130                 135                 140

Val Gln Thr Leu Gln Asp Pro Ser Lys Ala Leu Val Phe Glu Glu Ala
145                 150                 155                 160

Thr Leu Ser Trp Gln Gln Thr Cys Pro Gly Ile Val Asn Gly Ala Leu
                165                 170                 175

Glu Leu Glu Arg Asn Gly His Ala Ser Glu Gly Met Thr Arg Pro Arg
            180                 185                 190

Asp Ala Leu Gly Pro Glu Glu Gly Asn Ser Leu Gly Pro Glu Leu
        195                 200                 205

His Lys Ile Asn Leu Val Val Ser Lys Gly Met Met Leu Gly Val Cys
    210                 215                 220

Gly Asn Thr Gly Ser Gly Lys Ser Ser Leu Leu Ser Ala Ile Leu Glu
225                 230                 235                 240

Glu Met His Leu Leu Glu Gly Ser Val Gly Val Gln Gly Ser Leu Ala
                245                 250                 255

Tyr Val Pro Gln Gln Ala Trp Ile Val Ser Gly Asn Ile Arg Glu Asn
            260                 265                 270

Ile Leu Met Gly Gly Ala Tyr Asp Lys Ala Arg Tyr Leu Gln Val Leu
        275                 280                 285

His Cys Cys Ser Leu Asn Arg Asp Leu Glu Leu Leu Pro Phe Gly Asp
    290                 295                 300

Met Thr Glu Ile Gly Glu Arg Gly Leu Asn Leu Ser Gly Gly Gln Lys
305                 310                 315                 320
```

-continued

Gln Arg Ile Ser Leu Ala Arg Ala Val Tyr Ser Asp Arg Gln Ile Tyr
              325                 330                 335

Leu Leu Asp Asp Pro Leu Ser Ala Val Asp Ala His Val Gly Lys His
              340                 345                 350

Ile Phe Glu Glu Cys Ile Lys Lys Thr Leu Arg Gly Lys Thr Val Val
              355                 360                 365

Leu Val Thr His Gln Leu Gln Tyr Leu Glu Phe Cys Gly Gln Ile Ile
              370                 375                 380

Leu Leu Glu Asn Gly Lys Ile Cys Glu Asn Gly Thr His Ser Glu Leu
385                 390                 395                 400

Met Gln Lys Lys Gly Lys Tyr Ala Gln Leu Ile Gln Lys Met His Lys
              405                 410                 415

Glu Ala Thr Ser Asp Met Leu Gln Asp Thr Ala Lys Ile Ala Glu Lys
              420                 425                 430

Pro Lys Val Glu Ser Gln Ala Leu Ala Thr Ser Leu Glu Glu Ser Leu
              435                 440                 445

Asn Gly Asn Ala Val Pro Glu His Gln Leu Thr Gln Glu Glu Glu Met
450                 455                 460

Glu Glu Gly Ser Leu Ser Trp Arg Val Tyr His His Tyr Ile Gln Ala
465                 470                 475                 480

Ala Gly Gly Tyr Met Val Ser Cys Ile Ile Phe Phe Val Val Leu
              485                 490                 495

Ile Val Phe Leu Thr Ile Phe Ser Phe Trp Trp Leu Ser Tyr Trp Leu
              500                 505                 510

Glu Gln Gly Ser Gly Thr Asn Ser Ser Arg Glu Ser Asn Gly Thr Met
              515                 520                 525

Ala Asp Leu Gly Asn Ile Ala Asp Asn Pro Gln Leu Ser Phe Tyr Gln
              530                 535                 540

Leu Val Tyr Gly Leu Asn Ala Leu Leu Leu Ile Cys Val Gly Val Cys
545                 550                 555                 560

Ser Ser Gly Ile Phe Thr Lys Val Thr Arg Lys Ala Ser Thr Ala Leu
              565                 570                 575

His Asn Lys Leu Phe Asn Lys Val Phe Arg Cys Pro Met Ser Phe Phe
              580                 585                 590

Asp Thr Ile Pro Ile Gly Arg Leu Leu Asn Cys Phe Ala Gly Asp Leu
              595                 600                 605

Glu Gln Leu Asp Gln Leu Leu Pro Ile Phe Ser Glu Gln Phe Leu Val
              610                 615                 620

Leu Ser Leu Met Val Ile Ala Val Leu Leu Ile Val Ser Val Leu Ser
625                 630                 635                 640

Pro Tyr Ile Leu Leu Met Gly Ala Ile Ile Met Val Ile Cys Phe Ile
              645                 650                 655

Tyr Tyr Met

<210> SEQ ID NO 3
<211> LENGTH: 2115
<212> TYPE: DNA
<213> ORGANISM: homo sapiens

<400> SEQUENCE: 3
atgacaagaa tggctgtgaa ggctcagcat cacacatctg aggtcagcga ccagcgcatc      60
cgtgtgacca gtgaagttct cacttgcatt aagctgatta aaatgtacac atgggagaaa     120
ccatttgcaa aaatcattga agacctaaga aggaaggaaa ggaagctatt ggagaagtgc     180

-continued

```
gggcttgtcc agagcctgac aagtataacc ttgttcatca tccccacagt ggccacagcg      240
gtctgggttc tcatccacac atccttaaag ctgaaactca cagcgtcaat ggccttcagc      300
atgctggcct ccttgaatct ccttcggctg tcagtgttct ttgtgcctat tgcagtcaaa      360 gtctcacga attccaagtc tgcagtgatg aggttcaaga agttttttcct ccaggagagc      420 cctgttttct atgtccagac attacaagac cccagcaaag ctctggtctt tgaggaggcc      480
accttgtcat ggcaacagac ctgtcccggg atcgtcaatg ggcactgga gctggagagg      540 aacgggcatg cttctgaggg gatgaccagg cctagagatg ccctcgggcc agaggaagaa      600
gggaacagcc tgggcccaga gttgcacaag atcaacctgg tggtgtccaa ggggatgatg      660 ttagggtct gcggcaacac ggggagtggt aagagcagcc tgttgtcagc atcctggag      720 gagatgcact gctcgaggg ctcggtgggg gtgcagggaa gcctggccta tgtcccccag      780
caggcctgga tcgtcagcgg gaacatcagg gagaacatcc tcatgggagg cgcatatgac      840
aaggcccgat acctccaggt gctccactgc tgctccctga tcgggacct ggaacttctg      900 cccttttggag acatgacaga gattggagag cggggcctca acctctctgg ggggcagaaa      960
cagaggatca gcctggcccg cgccgtctat tccgaccgtc agatctacct gctggacgac     1020
cccctgtctg ctgtggacgc ccacgtgggg aagcacattt ttgaggagtg cattaagaag     1080
acactcaggg ggaagacggt cgtcctggtg acccaccagc tgcagtactt agaattttgt     1140
ggccagatca ttttgttgga aaatgggaaa atctgtgaaa atggaactca cagtgagtta     1200
atgcagaaaa aggggaaata tgcccaactt atccagaaga tgcacaagga agccacttcg     1260
gacatgttgc aggacacagc aaagatagca gagaagccaa aggtagaaag tcaggctctg     1320
gccacctccc tggaagagtc tctcaacgga aatgctgtgc cggagcatca gctcacacag     1380
gaggaggaga tggaagaagg ctccttgagt tggagggtct accaccacta catccaggca     1440
gctggaggtt acatggtctc ttgcataatt ttcttcttcg tggtgctgat cgtcttctta     1500
acgatcttca gcttctggtg gctgagctac tggttggagc agggctcggg gaccaatagc     1560
agccgagaga gcaatggaac catggcagac ctgggcaaca ttgcagacaa tcctcaactg     1620
tccttctacc agctggtgta cgggctcaac gccctgctcc tcatctgtgt gggggtctgc     1680
tcctcaggga ttttcaccaa ggtcacgagg aaggcatcca cggccctgca caacaagctc     1740
ttcaacaagg ttttccgctg ccccatgagt ttctttgaca ccatcccaat aggccggctt     1800
ttgaactgct tcgcagggga cttggaacag ctggaccagc tcttgcccat cttttcagag     1860
cagttcctgg tcctgtcctt aatggtgatc gccgtcctgt tgattgtcag tgtgctgtct     1920
ccatatatcc tgttaatggg agccataatc atggttattt gcttcattta ttatatgatg     1980
ttcaagaagg ccatcggtgt gttcaagaga ctggagaact atagccggtc tccttattc      2040 tcccacatcc tcaattctct gcaaggcctg agctccatcc atgtctatgg aaaaactgaa     2100
gacttcatca gccag                                                     2115
```

<210> SEQ ID NO 4
<211> LENGTH: 705
<212> TYPE: PRT
<213> ORGANISM: homo sapiens

<400> SEQUENCE: 4

```
Met Thr Arg Met Ala Val Lys Ala Gln His His Thr Ser Glu Val Ser
 1               5                  10                  15

Asp Gln Arg Ile Arg Val Thr Ser Glu Val Leu Thr Cys Ile Lys Leu
            20                  25                  30
```

```
Ile Lys Met Tyr Thr Trp Glu Lys Pro Phe Ala Lys Ile Ile Glu Asp
         35                  40                  45

Leu Arg Arg Lys Glu Arg Lys Leu Leu Glu Lys Cys Gly Leu Val Gln
         50                  55                  60

Ser Leu Thr Ser Ile Thr Leu Phe Ile Ile Pro Thr Val Ala Thr Ala
 65                  70                  75                  80

Val Trp Val Leu Ile His Thr Ser Leu Lys Leu Lys Leu Thr Ala Ser
                     85                  90                  95

Met Ala Phe Ser Met Leu Ala Ser Leu Asn Leu Leu Arg Leu Ser Val
                100                 105                 110

Phe Phe Val Pro Ile Ala Val Lys Gly Leu Thr Asn Ser Lys Ser Ala
                115                 120                 125

Val Met Arg Phe Lys Lys Phe Leu Gln Glu Ser Pro Val Phe Tyr
                130                 135                 140

Val Gln Thr Leu Gln Asp Pro Ser Lys Ala Leu Val Phe Glu Glu Ala
145                 150                 155                 160

Thr Leu Ser Trp Gln Gln Thr Cys Pro Gly Ile Val Asn Gly Ala Leu
                    165                 170                 175

Glu Leu Glu Arg Asn Gly His Ala Ser Glu Gly Met Thr Arg Pro Arg
                180                 185                 190

Asp Ala Leu Gly Pro Glu Glu Gly Asn Ser Leu Gly Pro Glu Leu
                195                 200                 205

His Lys Ile Asn Leu Val Val Ser Lys Gly Met Met Leu Gly Val Cys
                210                 215                 220

Gly Asn Thr Gly Ser Gly Lys Ser Ser Leu Leu Ser Ala Ile Leu Glu
225                 230                 235                 240

Glu Met His Leu Leu Glu Gly Ser Val Gly Val Gln Gly Ser Leu Ala
                    245                 250                 255

Tyr Val Pro Gln Gln Ala Trp Ile Val Ser Gly Asn Ile Arg Glu Asn
                260                 265                 270

Ile Leu Met Gly Gly Ala Tyr Asp Lys Ala Arg Tyr Leu Gln Val Leu
                275                 280                 285

His Cys Cys Ser Leu Asn Arg Asp Leu Glu Leu Leu Pro Phe Gly Asp
                290                 295                 300

Met Thr Glu Ile Gly Glu Arg Gly Leu Asn Leu Ser Gly Gly Gln Lys
305                 310                 315                 320

Gln Arg Ile Ser Leu Ala Arg Ala Val Tyr Ser Asp Arg Gln Ile Tyr
                    325                 330                 335

Leu Leu Asp Asp Pro Leu Ser Ala Val Asp Ala His Val Gly Lys His
                340                 345                 350

Ile Phe Glu Glu Cys Ile Lys Lys Thr Leu Arg Gly Lys Thr Val Val
                355                 360                 365

Leu Val Thr His Gln Leu Gln Tyr Leu Glu Phe Cys Gly Gln Ile Ile
                370                 375                 380

Leu Leu Glu Asn Gly Lys Ile Cys Glu Asn Gly Thr His Ser Glu Leu
385                 390                 395                 400

Met Gln Lys Lys Gly Lys Tyr Ala Gln Leu Ile Gln Lys Met His Lys
                    405                 410                 415

Glu Ala Thr Ser Asp Met Leu Gln Asp Thr Ala Lys Ile Ala Glu Lys
                420                 425                 430

Pro Lys Val Glu Ser Gln Ala Leu Ala Thr Ser Leu Glu Glu Ser Leu
                435                 440                 445
```

-continued

```
Asn Gly Asn Ala Val Pro Glu His Gln Leu Thr Gln Glu Glu Met
        450                 455                 460
Glu Glu Gly Ser Leu Ser Trp Arg Val Tyr His Tyr Ile Gln Ala
465                 470                 475                 480
Ala Gly Gly Tyr Met Val Ser Cys Ile Ile Phe Phe Val Val Leu
                485                 490                 495
Ile Val Phe Leu Thr Ile Phe Ser Phe Trp Trp Leu Ser Tyr Trp Leu
            500                 505                 510
Glu Gln Gly Ser Gly Thr Asn Ser Ser Arg Glu Ser Asn Gly Thr Met
            515                 520                 525
Ala Asp Leu Gly Asn Ile Ala Asp Asn Pro Gln Leu Ser Phe Tyr Gln
        530                 535                 540
Leu Val Tyr Gly Leu Asn Ala Leu Leu Leu Ile Cys Val Gly Val Cys
545                 550                 555                 560
Ser Ser Gly Ile Phe Thr Lys Val Thr Arg Lys Ala Ser Thr Ala Leu
                565                 570                 575
His Asn Lys Leu Phe Asn Lys Val Phe Arg Cys Pro Met Ser Phe Phe
            580                 585                 590
Asp Thr Ile Pro Ile Gly Arg Leu Leu Asn Cys Phe Ala Gly Asp Leu
        595                 600                 605
Glu Gln Leu Asp Gln Leu Leu Pro Ile Phe Ser Glu Gln Phe Leu Val
    610                 615                 620
Leu Ser Leu Met Val Ile Ala Val Leu Leu Ile Val Ser Val Leu Ser
625                 630                 635                 640
Pro Tyr Ile Leu Leu Met Gly Ala Ile Ile Met Val Ile Cys Phe Ile
                645                 650                 655
Tyr Tyr Met Met Phe Lys Lys Ala Ile Gly Val Phe Lys Arg Leu Glu
            660                 665                 670
Asn Tyr Ser Arg Ser Pro Leu Phe Ser His Ile Leu Asn Ser Leu Gln
        675                 680                 685
Gly Leu Ser Ser Ile His Val Tyr Gly Lys Thr Glu Asp Phe Ile Ser
    690                 695                 700
Gln
705

<210> SEQ ID NO 5
<211> LENGTH: 3189
<212> TYPE: DNA
<213> ORGANISM: homo sapiens

<400> SEQUENCE: 5
atgacaagaa tggctgtgaa ggctcagcat cacacatctg aggtcagcga ccagcgcatc      60
cgtgtgacca gtgaagttct cacttgcatt aagctgatta aaatgtacac atgggagaaa     120
ccatttgcaa aaatcattga agacctaaga aggaaggaaa ggaagctatt ggagaagtgc     180
gggcttgtcc agagcctgac aagtataacc ttgttcatca tccccacagt ggccacagcg     240
gtctgggttc tcatccacac atccttaaag ctgaaactca cagcgtcaat ggccttcagc     300
atgctggcct ccttgaatct ccttcggctg tcagtgttct tgtgcctat tgcagtcaaa     360 ggtctcacga attccaagtc tgcagtgatg aggttcaaga agttttttcct ccaggagagc     420 cctgtttttct atgtccagac attacaagac cccagcaaag ctctggtctt tgaggaggcc     480
accttgtcat ggcaacagac ctgtcccggg atcgtcaatg ggcactgga gctggagagg     540 aacgggcatg cttctgaggg gatgaccagg cctagagatg ccctcgggcc agaggaagaa     600
```

```
gggaacagcc tgggcccaga gttgcacaag atcaacctgg tggtgtccaa ggggatgatg      660 ttagggtct  gcggcaacac ggggagtggt aagagcagcc tgttgtcagc catcctggag      720
gagatgcact tgctcgaggg ctcggtgggg gtgcagggaa gcctggccta tgtcccccag      780
caggcctgga tcgtcagcgg gaacatcagg gagaacatcc tcatgggagg cgcatatgac      840
aaggcccgat acctccaggt gctccactgc tgctccctga atcgggacct ggaacttctg      900
cccctttgga gacatgacag agattggaga gcggggcctca acctctctgg ggggcagaaa    960
cagaggatca gcctggcccg cgccgtctat tccgaccgtc agatctacct gctggacgac     1020
cccctgtctg ctgtggacgc ccacgtgggg aagcacattt tgaggagtg  cattaagaag     1080 acactcaggg ggaagacggt cgtcctggtg acccaccagc tgcagtactt agaattttgt     1140
ggccagatca ttttgttgga aaatgggaaa atctgtgaaa atggaactca cagtgagtta     1200
atgcagaaaa aggggaaata tgcccaactt atccagaaga tgcacaagga agccacttcg     1260
gacatgttgc aggacacagc aaagatagca gagaagccaa aggtagaaag tcaggctctg     1320
gccacctccc tggaagagtc tctcaacgga aatgctgtgc cggagcatca gctcacacag     1380
gaggaggaga tggaagaagg ctccttgagt tggagggtct accaccacta catccaggca     1440
gctggaggtt acatggtctc ttgcataatt ttcttcttcg tggtgctgat cgtcttctta     1500
acgatcttca gcttctggtg gctgagctac tggttggagc agggctcggg gaccaatagc     1560
agccgagaga gcaatggaac catggcagac ctgggcaaca ttgcagacaa tcctcaactg     1620
tccttctacc agctggtgta cgggctcaac gccctgctcc tcatctgtgt gggggtctgc     1680
tcctcaggga ttttcaccaa ggtcacgagg aaggcatcca cggccctgca caacaagctc     1740
ttcaacaagg ttttccgctg ccccatgagt ttctttgaca ccatcccaat aggccggctt     1800
ttgaactgct tcgcagggga cttggaacag ctggaccagc tcttgcccat cttttcagag     1860
cagttcctgg tcctgtcctt aatggtgatc gccgtcctgt tgattgtcag tgtgctgtct     1920
ccatatatcc tgttaatggg agccataatc atggttattt gcttcattta ttatatgatg     1980
ttcaagaagg ccatcggtgt gttcaagaga ctggagaact atagccggtc tcctttattc     2040
tcccacatcc tcaattctct gcaaggcctg agctccatcc atgtctatgg aaaaactgaa     2100
gacttcatca gccagtttaa gaggctgact gatgcgcaga ataactacct gctgttgttt     2160
ctatcttcca cacgatggat ggcattgagg ctggagatca tgaccaacct tgtgaccttg     2220
gctgttgccc tgttcgtggc ttttggcatt tcctccaccc cctactcctt taaagtcatg     2280
gctgtcaaca tcgtgctgca gctggcgtcc agcttccagg ccactgcccg gattggcttg     2340
gagacagagg cacagttcac ggctgtagag aggatactgc agtacatgaa gatgtgtgtc     2400
tcggaagctc ctttacacat ggaaggcaca agttgtcccc aggggtggcc acagcatggg     2460
gaaatcatat ttcaggatta tcacatgaaa tacagagaca acacacccac cgtgcttcac     2520
ggcatcaacc tgaccatccg cggccacgaa gtggtgggca tcgtgggaag gacgggctct     2580
gggaagtcct ccttgggcat ggctctcttc cgcctggtgg agcccatggc aggccggatt     2640
ctcattgacg gcgtggacat ttgcagcatc ggcctggagg acttgcggtc caagctctca     2700
gtgatccctc aagatccagt gctgctctca ggaaccatca gattcaacct agatcccttt     2760
gaccgtcaca ctgaccagca gatctgggat gccttggaga ggacattcct gaccaaggcc     2820
atctcaaagt tccccaaaaa gctgcataca gatgtggtgg aaaacggtgg aaacttctct     2880
gtgggggaga ggcagctgct ctgcattgcc agggctgtgc ttcgcaactc caagatcatc     2940
cttatcgatg aagccacagc ctccattgac atggagacag acaccctgat ccagcgcaca     3000
```

```
atccgtgaag ccttccaggg ctgcaccgtg ctcgtcattg cccaccgtgt caccactgtg    3060
ctgaactgtg accacatcct ggttatgggc aatgggaagg tggtagaatt tgatcggccg    3120
gaggtactgc ggaagaagcc tgggtcattg ttcgcagccc tcatggccac agccacttct    3180
tcactgaga                                                              3189

<210> SEQ ID NO 6
<211> LENGTH: 1063
<212> TYPE: PRT
<213> ORGANISM: homo sapiens

<400> SEQUENCE: 6
```

Met Thr Arg Met Ala Val Lys Ala Gln His His Thr Ser Glu Val Ser
 1               5                  10                  15

Asp Gln Arg Ile Arg Val Thr Ser Glu Val Leu Thr Cys Ile Lys Leu
            20                  25                  30

Ile Lys Met Tyr Thr Trp Glu Lys Pro Phe Ala Lys Ile Glu Asp
        35                  40                  45

Leu Arg Arg Lys Glu Arg Lys Leu Leu Glu Lys Cys Gly Leu Val Gln
50                  55                  60

Ser Leu Thr Ser Ile Thr Leu Phe Ile Pro Thr Val Ala Thr Ala
65                  70                  75                  80

Val Trp Val Leu Ile His Thr Ser Leu Lys Leu Lys Leu Thr Ala Ser
                85                  90                  95

Met Ala Phe Ser Met Leu Ala Ser Leu Asn Leu Leu Arg Leu Ser Val
            100                 105                 110

Phe Phe Val Pro Ile Ala Val Lys Gly Leu Thr Asn Ser Lys Ser Ala
        115                 120                 125

Val Met Arg Phe Lys Lys Phe Phe Leu Gln Glu Ser Pro Val Phe Tyr
130                 135                 140

Val Gln Thr Leu Gln Asp Pro Ser Lys Ala Leu Val Phe Glu Glu Ala
145                 150                 155                 160

Thr Leu Ser Trp Gln Gln Thr Cys Pro Gly Ile Val Asn Gly Ala Leu
                165                 170                 175

Glu Leu Glu Arg Asn Gly His Ala Ser Glu Gly Met Thr Arg Pro Arg
            180                 185                 190

Asp Ala Leu Gly Pro Glu Glu Glu Gly Asn Ser Leu Gly Pro Glu Leu
        195                 200                 205

His Lys Ile Asn Leu Val Val Ser Lys Gly Met Met Leu Gly Val Cys
210                 215                 220

Gly Asn Thr Gly Ser Gly Lys Ser Ser Leu Leu Ser Ala Ile Leu Glu
225                 230                 235                 240

Glu Met His Leu Leu Glu Gly Ser Val Gly Val Gln Gly Ser Leu Ala
                245                 250                 255

Tyr Val Pro Gln Gln Ala Trp Ile Val Ser Gly Asn Ile Arg Glu Asn
            260                 265                 270

Ile Leu Met Gly Gly Ala Tyr Asp Lys Ala Arg Tyr Leu Gln Val Leu
        275                 280                 285

His Cys Cys Ser Leu Asn Arg Asp Leu Glu Leu Leu Pro Phe Gly Asp
290                 295                 300

Met Thr Glu Ile Gly Glu Arg Gly Leu Asn Leu Ser Gly Gly Gln Lys
305                 310                 315                 320

Gln Arg Ile Ser Leu Ala Arg Ala Val Tyr Ser Asp Arg Gln Ile Tyr
                325                 330                 335

-continued

```
Leu Leu Asp Asp Pro Leu Ser Ala Val Asp Ala His Val Gly Lys His
            340                 345                 350
Ile Phe Glu Glu Cys Ile Lys Lys Thr Leu Arg Gly Lys Thr Val Val
        355                 360                 365
Leu Val Thr His Gln Leu Gln Tyr Leu Glu Phe Cys Gly Gln Ile Ile
    370                 375                 380
Leu Leu Glu Asn Gly Lys Ile Cys Glu Asn Gly Thr His Ser Glu Leu
385                 390                 395                 400
Met Gln Lys Lys Gly Lys Tyr Ala Gln Leu Ile Gln Lys Met His Lys
            405                 410                 415
Glu Ala Thr Ser Asp Met Leu Gln Asp Thr Ala Lys Ile Ala Glu Lys
        420                 425                 430
Pro Lys Val Glu Ser Gln Ala Leu Ala Thr Ser Leu Glu Glu Ser Leu
    435                 440                 445
Asn Gly Asn Ala Val Pro Glu His Gln Leu Thr Gln Glu Glu Glu Met
450                 455                 460
Glu Glu Gly Ser Leu Ser Trp Arg Val Tyr His His Tyr Ile Gln Ala
465                 470                 475                 480
Ala Gly Gly Tyr Met Val Ser Cys Ile Ile Phe Phe Val Val Leu
            485                 490                 495
Ile Val Phe Leu Thr Ile Phe Ser Phe Trp Trp Leu Ser Tyr Trp Leu
        500                 505                 510
Glu Gln Gly Ser Gly Thr Asn Ser Ser Arg Glu Ser Asn Gly Thr Met
    515                 520                 525
Ala Asp Leu Gly Asn Ile Ala Asp Asn Pro Gln Leu Ser Phe Tyr Gln
530                 535                 540
Leu Val Tyr Gly Leu Asn Ala Leu Leu Leu Ile Cys Val Gly Val Cys
545                 550                 555                 560
Ser Ser Gly Ile Phe Thr Lys Val Thr Arg Lys Ala Ser Thr Ala Leu
            565                 570                 575
His Asn Lys Leu Phe Asn Lys Val Phe Arg Cys Pro Met Ser Phe Phe
        580                 585                 590
Asp Thr Ile Pro Ile Gly Arg Leu Leu Asn Cys Phe Ala Gly Asp Leu
    595                 600                 605
Glu Gln Leu Asp Gln Leu Leu Pro Ile Phe Ser Glu Gln Phe Leu Val
610                 615                 620
Leu Ser Leu Met Val Ile Ala Val Leu Leu Ile Val Ser Val Leu Ser
625                 630                 635                 640
Pro Tyr Ile Leu Leu Met Gly Ala Ile Ile Met Val Ile Cys Phe Ile
            645                 650                 655
Tyr Tyr Met Met Phe Lys Lys Ala Ile Gly Val Phe Lys Arg Leu Glu
        660                 665                 670
Asn Tyr Ser Arg Ser Pro Leu Phe Ser His Ile Leu Asn Ser Leu Gln
    675                 680                 685
Gly Leu Ser Ser Ile His Val Tyr Gly Lys Thr Glu Asp Phe Ile Ser
690                 695                 700
Gln Phe Lys Arg Leu Thr Asp Ala Gln Asn Asn Tyr Leu Leu Leu Phe
705                 710                 715                 720
Leu Ser Ser Thr Arg Trp Met Ala Leu Arg Leu Glu Ile Met Thr Asn
            725                 730                 735
Leu Val Thr Leu Ala Val Ala Leu Phe Val Ala Phe Gly Ile Ser Ser
        740                 745                 750
```

```
Thr Pro Tyr Ser Phe Lys Val Met Ala Val Asn Ile Val Leu Gln Leu
        755                 760                 765

Ala Ser Ser Phe Gln Ala Thr Ala Arg Ile Gly Leu Glu Thr Glu Ala
        770                 775                 780

Gln Phe Thr Ala Val Glu Arg Ile Leu Gln Tyr Met Lys Met Cys Val
785                 790                 795                 800

Ser Glu Ala Pro Leu His Met Glu Gly Thr Ser Cys Pro Gln Gly Trp
                805                 810                 815

Pro Gln His Gly Glu Ile Ile Phe Gln Asp Tyr His Met Lys Tyr Arg
                820                 825                 830

Asp Asn Thr Pro Thr Val Leu His Gly Ile Asn Leu Thr Ile Arg Gly
            835                 840                 845

His Glu Val Val Gly Ile Val Gly Arg Thr Gly Ser Gly Lys Ser Ser
    850                 855                 860

Leu Gly Met Ala Leu Phe Arg Leu Val Glu Pro Met Ala Gly Arg Ile
865                 870                 875                 880

Leu Ile Asp Gly Val Asp Ile Cys Ser Ile Gly Leu Glu Asp Leu Arg
                885                 890                 895

Ser Lys Leu Ser Val Ile Pro Gln Asp Pro Val Leu Leu Ser Gly Thr
                900                 905                 910

Ile Arg Phe Asn Leu Asp Pro Phe Asp Arg His Thr Asp Gln Gln Ile
            915                 920                 925

Trp Asp Ala Leu Glu Arg Thr Phe Leu Thr Lys Ala Ile Ser Lys Phe
    930                 935                 940

Pro Lys Lys Leu His Thr Asp Val Val Glu Asn Gly Gly Asn Phe Ser
945                 950                 955                 960

Val Gly Glu Arg Gln Leu Leu Cys Ile Ala Arg Ala Val Leu Arg Asn
                965                 970                 975

Ser Lys Ile Ile Leu Ile Asp Glu Ala Thr Ala Ser Ile Asp Met Glu
            980                 985                 990

Thr Asp Thr Leu Ile Gln Arg Thr Ile Arg Glu Ala Phe Gln Gly Cys
    995                 1000                1005

Thr Val Leu Val Ile Ala His Arg Val Thr Thr Val Leu Asn Cys Asp
        1010                1015                1020

His Ile Leu Val Met Gly Asn Gly Lys Val Val Glu Phe Asp Arg Pro
1025                1030                1035                1040

Glu Val Leu Arg Lys Lys Pro Gly Ser Leu Phe Ala Ala Leu Met Ala
                1045                1050                1055

Thr Ala Thr Ser Ser Leu Arg
            1060

<210> SEQ ID NO 7
<211> LENGTH: 1488
<212> TYPE: DNA
<213> ORGANISM: homo sapiens

<400> SEQUENCE: 7
atgacaagaa tggctgtgaa ggctcagcat cacacatctg aggtcagcga ccagcgcatc    60
cgtgtgacca gtgaagttct cacttgcatt aagctgatta aaatgtacac atgggagaaa   120
ccatttgcaa aaatcattga agacctaaga aggaaggaaa ggaagctatt ggagaagtgc   180
gggcttgtcc agagcctgac aagtataacc ttgttcatca tccccacagt ggccacagcg   240
gtctgggttc tcatccacac atccttaaag ctgaaactca cagcgtcaat ggccttcagc   300
atgctggcct ccttgaatct ccttcggctg tcagtgttct ttgtgcctat tgcagtcaaa   360
```

-continued

```
ggtctcacga attccaagtc tgcagtgatg aggttcaaga agttttcct ccaggagagc      420 cctgttttct atgtccagac attacaagac cccagcaaag ctctggtctt tgaggaggcc      480
accttgtcat ggcaacagac ctgtcccggg atcgtcaatg ggcactgga gctggagagg      540 aacgggcatg cttctgaggg gatgaccagg cctagagatg ccctcgggcc agaggaagaa      600
gggaacagcc tgggcccaga gttgcacaag atcaacctgg tggtgtccaa ggggatgatg      660 ttagggtct  gcggcaacac ggggagtggt aagagcagcc tgttgtcagc catcctggag      720
gagatgcact tgctcgaggg ctcggtgggg gtgcagggaa gcctggccta tgtcccccag      780
caggcctgga tcgtcagcgg gaacatcagg gagaacatcc tcatgggagg cgcatatgac      840
aaggcccgat acctccaggt gctccactgc tgctccctga tcgggacct  ggaacttctg      900 cccttttggag acatgacaga gattggagag cggggcctca acctctctgg ggggcagaaa      960
cagaggatca gcctggcccg cgccgtctat tccgaccgtc agatctacct gctggacgac     1020 ccctgtctg ctgtggacgc ccacgtgggg aagcacattt ttgaggagtg cattaagaag     1080
acactcaggg ggaagacggt cgtcctggtg acccaccagc tgcagtactt agaattttgt     1140
ggccagatca ttttgttgga aaatgggaaa atctgtgaaa atggaactca cagtgagtta     1200
atgcagaaaa agggaaata  tgcccaactt atccagaaga tgcacaagga agccacttcg     1260
gttttccgct gccccatgag tttctttgac accatcccaa taggccggct tttgaactgc     1320
ttcgcagggg acttggaaca gctggaccag ctcttgccca tcttttcaga gcagttcctg     1380
gtcctgtcct taatggtgat cgccgtcctg ttgattgtca gtgtgctgtc tccatatatc     1440
ctgttaatgg gagccataat catggttatt tgcttcattt attatatg                  1488
```

<210> SEQ ID NO 8
<211> LENGTH: 496
<212> TYPE: PRT
<213> ORGANISM: homo sapiens

<400> SEQUENCE: 8

```
Met Thr Arg Met Ala Val Lys Ala Gln His His Thr Ser Glu Val Ser
  1               5                  10                  15

Asp Gln Arg Ile Arg Val Thr Ser Glu Val Leu Thr Cys Ile Lys Leu
             20                  25                  30

Ile Lys Met Tyr Thr Trp Glu Lys Pro Phe Ala Lys Ile Ile Glu Asp
         35                  40                  45

Leu Arg Arg Lys Glu Arg Lys Leu Leu Glu Lys Cys Gly Leu Val Gln
     50                  55                  60

Ser Leu Thr Ser Ile Thr Leu Phe Ile Ile Pro Thr Val Ala Thr Ala
 65                  70                  75                  80

Val Trp Val Leu Ile His Thr Ser Leu Lys Leu Lys Leu Thr Ala Ser
                 85                  90                  95

Met Ala Phe Ser Met Leu Ala Ser Leu Asn Leu Arg Leu Ser Val
                100                 105                 110

Phe Phe Val Pro Ile Ala Val Lys Gly Leu Thr Asn Ser Lys Ser Ala
            115                 120                 125

Val Met Arg Phe Lys Lys Phe Phe Leu Gln Glu Ser Pro Val Phe Tyr
        130                 135                 140

Val Gln Thr Leu Gln Asp Pro Ser Lys Ala Leu Val Phe Glu Glu Ala
145                 150                 155                 160

Thr Leu Ser Trp Gln Gln Thr Cys Pro Gly Ile Val Asn Gly Ala Leu
                165                 170                 175
```

```
Glu Leu Glu Arg Asn Gly His Ala Ser Glu Gly Met Thr Arg Pro Arg
            180                 185                 190
Asp Ala Leu Gly Pro Glu Glu Gly Asn Ser Leu Gly Pro Glu Leu
        195                 200                 205
His Lys Ile Asn Leu Val Val Ser Lys Gly Met Met Leu Gly Val Cys
    210                 215                 220
Gly Asn Thr Gly Ser Gly Lys Ser Ser Leu Leu Ser Ala Ile Leu Glu
225                 230                 235                 240
Glu Met His Leu Leu Glu Gly Ser Val Gly Val Gln Gly Ser Leu Ala
                245                 250                 255
Tyr Val Pro Gln Gln Ala Trp Ile Val Ser Gly Asn Ile Arg Glu Asn
            260                 265                 270
Ile Leu Met Gly Gly Ala Tyr Asp Lys Ala Arg Tyr Leu Gln Val Leu
        275                 280                 285
His Cys Cys Ser Leu Asn Arg Asp Leu Glu Leu Leu Pro Phe Gly Asp
    290                 295                 300
Met Thr Glu Ile Gly Glu Arg Gly Leu Asn Leu Ser Gly Gly Gln Lys
305                 310                 315                 320
Gln Arg Ile Ser Leu Ala Arg Ala Val Tyr Ser Asp Arg Gln Ile Tyr
                325                 330                 335
Leu Leu Asp Asp Pro Leu Ser Ala Val Asp Ala His Val Gly Lys His
            340                 345                 350
Ile Phe Glu Glu Cys Ile Lys Lys Thr Leu Arg Gly Lys Thr Val Val
        355                 360                 365
Leu Val Thr His Gln Leu Gln Tyr Leu Glu Phe Cys Gly Gln Ile Ile
    370                 375                 380
Leu Leu Glu Asn Gly Lys Ile Cys Glu Asn Gly Thr His Ser Glu Leu
385                 390                 395                 400
Met Gln Lys Lys Gly Lys Tyr Ala Gln Leu Ile Gln Lys Met His Lys
                405                 410                 415
Glu Ala Thr Ser Val Phe Arg Cys Pro Met Ser Phe Phe Asp Thr Ile
            420                 425                 430
Pro Ile Gly Arg Leu Leu Asn Cys Phe Ala Gly Asp Leu Glu Gln Leu
        435                 440                 445
Asp Gln Leu Leu Pro Ile Phe Ser Glu Gln Phe Leu Val Leu Ser Leu
    450                 455                 460
Met Val Ile Ala Val Leu Leu Ile Val Ser Val Leu Ser Pro Tyr Ile
465                 470                 475                 480
Leu Leu Met Gly Ala Ile Ile Met Val Ile Cys Phe Ile Tyr Tyr Met
                485                 490                 495

<210> SEQ ID NO 9
<211> LENGTH: 1626
<212> TYPE: DNA
<213> ORGANISM: homo sapiens

<400> SEQUENCE: 9
atgacaagaa tggctgtgaa ggctcagcat cacacatctg aggtcagcga ccagcgcatc        60
cgtgtgacca gtgaagttct cacttgcatt aagctgatta aaatgtacac atggagaaaa       120
ccatttgcaa aaatcattga agacctaaga aggaaggaaa ggaagctatt ggagaagtgc       180
gggcttgtcc agagcctgac aagtataacc ttgttcatca tccccacagt ggccacagcg       240
gtctgggttc tcatccacac atccttaaag ctgaaactca cagcgtcaat ggccttcagc       300
```

```
atgctggcct ccttgaatct ccttcggctg tcagtgttct ttgtgcctat tgcagtcaaa    360
ggtctcacga attccaagtc tgcagtgatg aggttcaaga agttttttcct ccaggagagc   420 cctgttttct atgtccagac attacaagac cccagcaaag ctctggtctt tgaggaggcc    480
accttgtcat ggcaacagac ctgtcccggg atcgtcaatg ggcactgga gctggagagg    540 aacgggcatg cttctgaggg gatgaccagg cctagagatg ccctcgggcc agaggaagaa    600
gggaacagcc tgggcccaga gttgcacaag atcaacctgg tggtgtccaa ggggatgatg    660 ttagggtct gcggcaacac ggggagtggt aagagcagcc tgttgtcagc catcctggag    720
gagatgcact tgctcgaggg ctcggtgggg gtgcagggaa gcctggccta tgtcccccag    780
caggcctgga tcgtcagcgg gaacatcagg gagaacatcc tcatgggagg cgcatatgac    840
aaggcccgat acctccaggt gctccactgc tgctccctga tcgggacct ggaacttctg    900 cccttttgga catgacaga gattggagag cggggcctca acctctctgg ggggcagaaa    960
cagaggatca gcctggcccg cgccgtctat tccgaccgtc agatctacct gctggacgac   1020
cccctgtctg ctgtggacgc ccacgtgggg aagcacattt ttgaggagtg cattaagaag   1080
acactcaggg ggaagacggt cgtcctggtg acccaccagc tgcagtactt agaattttgt   1140
ggccagatca tttgttgga aaatgggaaa atctgtgaaa atggaactca cagtgagtta   1200
atgcagaaaa aggggaaata tgcccaactt atccagaaga tgcacaagga agccacttcg   1260
gttttccgct gccccatgag tttctttgac accatcccaa taggccggct tttgaactgc   1320
ttcgcagggg acttggaaca gctggaccag ctcttgccca tcttttcaga gcagttcctg   1380
gtcctgtcct taatggtgat cgccgtcctg ttgattgtca gtgtgctgtc tccatatatc   1440
ctgttaatgg gagccataat catggttatt tgcttcattt attatatgat gttcaagaag   1500
gccatcggtg tgttcaagag actggagaac tatagccggt ctcctttatt ctcccacatc   1560
ctcaattctc tgcaaggcct gagctccatc catgtctatg gaaaaactga agacttcatc   1620
agccag                                                               1626
```

<210> SEQ ID NO 10
<211> LENGTH: 542
<212> TYPE: PRT
<213> ORGANISM: homo sapiens

<400> SEQUENCE: 10

```
Met Thr Arg Met Ala Val Lys Ala Gln His His Thr Ser Glu Val Ser
 1               5                  10                  15

Asp Gln Arg Ile Arg Val Thr Ser Glu Val Leu Thr Cys Ile Lys Leu
            20                  25                  30

Ile Lys Met Tyr Thr Trp Glu Lys Pro Phe Ala Lys Ile Ile Glu Asp
        35                  40                  45

Leu Arg Arg Lys Glu Arg Lys Leu Leu Glu Lys Cys Gly Leu Val Gln
    50                  55                  60

Ser Leu Thr Ser Ile Thr Leu Phe Ile Ile Pro Thr Val Ala Thr Ala
65                  70                  75                  80

Val Trp Val Leu Ile His Thr Ser Leu Lys Leu Lys Leu Thr Ala Ser
                85                  90                  95

Met Ala Phe Ser Met Leu Ala Ser Leu Asn Leu Leu Arg Leu Ser Val
            100                 105                 110

Phe Phe Val Pro Ile Ala Val Lys Gly Leu Thr Asn Ser Lys Ser Ala
        115                 120                 125

Val Met Arg Phe Lys Lys Phe Phe Leu Gln Glu Ser Pro Val Phe Tyr
```

-continued

```
            130                 135                 140
Val Gln Thr Leu Gln Asp Pro Ser Lys Ala Leu Val Phe Glu Glu Ala
145                 150                 155                 160

Thr Leu Ser Trp Gln Gln Thr Cys Pro Gly Ile Val Asn Gly Ala Leu
                165                 170                 175

Glu Leu Glu Arg Asn Gly His Ala Ser Glu Gly Met Thr Arg Pro Arg
                180                 185                 190

Asp Ala Leu Gly Pro Glu Glu Gly Asn Ser Leu Gly Pro Glu Leu
                195                 200                 205

His Lys Ile Asn Leu Val Val Ser Lys Gly Met Met Leu Gly Val Cys
        210                 215                 220

Gly Asn Thr Gly Ser Gly Lys Ser Ser Leu Leu Ser Ala Ile Leu Glu
225                 230                 235                 240

Glu Met His Leu Leu Glu Gly Ser Val Gly Val Gln Gly Ser Leu Ala
                245                 250                 255

Tyr Val Pro Gln Gln Ala Trp Ile Val Ser Gly Asn Ile Arg Glu Asn
                260                 265                 270

Ile Leu Met Gly Gly Ala Tyr Asp Lys Ala Arg Tyr Leu Gln Val Leu
        275                 280                 285

His Cys Cys Ser Leu Asn Arg Asp Leu Glu Leu Leu Pro Phe Gly Asp
        290                 295                 300

Met Thr Glu Ile Gly Glu Arg Gly Leu Asn Leu Ser Gly Gly Gln Lys
305                 310                 315                 320

Gln Arg Ile Ser Leu Ala Arg Ala Val Tyr Ser Asp Arg Gln Ile Tyr
                325                 330                 335

Leu Leu Asp Asp Pro Leu Ser Ala Val Asp Ala His Val Gly Lys His
                340                 345                 350

Ile Phe Glu Glu Cys Ile Lys Lys Thr Leu Arg Gly Lys Thr Val Val
            355                 360                 365

Leu Val Thr His Gln Leu Gln Tyr Leu Glu Phe Cys Gly Gln Ile Ile
        370                 375                 380

Leu Leu Glu Asn Gly Lys Ile Cys Glu Asn Gly Thr His Ser Glu Leu
385                 390                 395                 400

Met Gln Lys Lys Gly Lys Tyr Ala Gln Leu Ile Gln Lys Met His Lys
                405                 410                 415

Glu Ala Thr Ser Val Phe Arg Cys Pro Met Ser Phe Asp Thr Ile
                420                 425                 430

Pro Ile Gly Arg Leu Leu Asn Cys Phe Ala Gly Asp Leu Glu Gln Leu
            435                 440                 445

Asp Gln Leu Leu Pro Ile Phe Ser Glu Gln Phe Leu Val Leu Ser Leu
        450                 455                 460

Met Val Ile Ala Val Leu Leu Ile Val Ser Val Leu Ser Pro Tyr Ile
465                 470                 475                 480

Leu Leu Met Gly Ala Ile Ile Met Val Ile Cys Phe Ile Tyr Tyr Met
                485                 490                 495

Met Phe Lys Lys Ala Ile Gly Val Phe Lys Arg Leu Glu Asn Tyr Ser
                500                 505                 510

Arg Ser Pro Leu Phe Ser His Ile Leu Asn Ser Leu Gln Gly Leu Ser
            515                 520                 525

Ser Ile His Val Tyr Gly Lys Thr Glu Asp Phe Ile Ser Gln
        530                 535                 540
```

<210> SEQ ID NO 11

-continued

<211> LENGTH: 2700
<212> TYPE: DNA
<213> ORGANISM: homo sapiens

<400> SEQUENCE: 11

| | |
|---|---:|
| atgacaagaa tggctgtgaa ggctcagcat cacacatctg aggtcagcga ccagcgcatc | 60 |
| cgtgtgacca gtgaagttct cacttgcatt aagctgatta aaatgtacac atgggagaaa | 120 |
| ccatttgcaa aaatcattga agacctaaga aggaaggaaa ggaagctatt ggagaagtgc | 180 |
| gggcttgtcc agagcctgac aagtataacc ttgttcatca tccccacagt ggccacagcg | 240 |
| gtctgggttc tcatccacac atccttaaag ctgaaactca cagcgtcaat ggccttcagc | 300 |
| atgctggcct ccttgaatct ccttcggctg tcagtgttct tgtgcctat gcagtcaaa | 360 |
| ggtctcacga attccaagtc tgcagtgatg aggttcaaga agttttcct ccaggagagc | 420 |
| cctgttttct atgtccagac attacaagac cccagcaaag ctctggtctt tgaggaggcc | 480 |
| accttgtcat ggcaacagac ctgtcccggg atcgtcaatg gggcactgga gctggagagg | 540 |
| aacgggcatg cttctgaggg gatgaccagg cctagagatg ccctcgggcc agaggaagaa | 600 |
| gggaacagcc tgggcccaga gttgcacaag atcaacctgg tggtgtccaa ggggatgatg | 660 |
| ttagggtct gcggcaacac ggggagtggt aagagcagcc tgttgtcagc catcctggag | 720 |
| gagatgcact gctcgaggg ctcggtgggg gtgcagggaa gcctggccta tgtcccccag | 780 |
| caggcctgga tcgtcagcgg gaacatcagg gagaacatcc tcatgggagg cgcatatgac | 840 |
| aaggcccgat acctccaggt gctccactgc tgctccctga tcggggacct ggaacttctg | 900 |
| cccttggag acatgacaga gattggagag cggggcctca acctctctgg ggggcagaaa | 960 |
| cagaggatca gcctggcccg cgccgtctat tccgaccgtc agatctacct gctggacgac | 1020 |
| ccctgtctg ctgtggacgc ccacgtgggg aagcacattt tgaggagtg cattaagaag | 1080 |
| acactcaggg ggaagacggt cgtcctggtg acccaccagc tgcagtactt agaattttgt | 1140 |
| ggccagatca ttttgttgga aaatgggaaa atctgtgaaa atggaactca cagtgagtta | 1200 |
| atgcagaaaa agggaaata tgcccaactt atccagaaga tgcacaagga agccacttcg | 1260 |
| gttttccgct gccccatgag tttctttgac accatcccaa taggccggct tttgaactgc | 1320 |
| ttcgcagggg acttggaaca gctggaccag ctcttgccca tcttttcaga gcagttcctg | 1380 |
| gtcctgtcct taatggtgat cgccgtcctg ttgattgtca gtgtgctgtc tccatatatc | 1440 |
| ctgttaatgg gagccataat catgcttatt tgcttcattt attatatgat gttcaagaag | 1500 |
| gccatcggtg tgttcaagag actggagaac tatagccggt ctcctttatt ctcccacatc | 1560 |
| ctcaattctc tgcaaggcct gagctccatc catgtctatg aaaaactga agacttcatc | 1620 |
| agccagttta gaggctgac tgatgcgcag ataactacc tgctgttgtt tctatcttcc | 1680 |
| acacgatgga tggcattgag gctggagatc atgaccaacc ttgtgacctt ggctgttgcc | 1740 |
| ctgttcgtgg cttttggcat ttcctccacc ccctactcct ttaaagtcat ggctgtcaac | 1800 |
| atcgtgctgc agctggcgtc cagcttccag gccactgccc ggattggctt ggagacagag | 1860 |
| gcacagttca cggctgtaga gaggatactg cagtacatga agatgtgtgt ctcggaagct | 1920 |
| cctttacaca tggaaggcac aagttgtccc caggggtggc acagcatggg gaaatcata | 1980 |
| tttcaggatt atcacatgaa atacagagac aacacaccca ccgtgcttca cggcatcaac | 2040 |
| ctgaccatcc gcggccacga agtggtgggc atcgtgggaa ggacgggctc tgggaagtcc | 2100 |
| tccttgggca tggctctctt ccgcctggtg gagcccatgg caggccggat tctcattgac | 2160 |
| ggcgtggaca tttgcagcat cggcctggag gacttgcggt ccaagctctc agtgatccct | 2220 |

-continued

```
caagatccag tgctgctctc aggaaccatc agattcaacc tagatccctt tgaccgtcac    2280
actgaccagc agatctggga tgccttggag aggacattcc tgaccaaggc catctcaaag    2340
ttccccaaaa agctgcatac agatgtggtg gaaaacggtg gaaacttctc tgtgggggag    2400
aggcagctgc tctgcattgc cagggctgtg cttcgcaact ccaagatcat ccttatcgat    2460
gaagccacag cctccattga catggagaca gacaccctga tccagcgcac aatccgtgaa    2520
gccttccagg gctgcaccgt gctcgtcatt gcccaccgtg tcaccactgt gctgaactgt    2580
gaccacatcc tggttatggg caatgggaag gtggtagaat ttgatcggcc ggaggtactg    2640
cggaagaagc ctgggtcatt gttcgcagcc ctcatggcca cagccacttc ttcactgaga    2700
```

<210> SEQ ID NO 12
<211> LENGTH: 900
<212> TYPE: PRT
<213> ORGANISM: homo sapiens

<400> SEQUENCE: 12

```
Met Thr Arg Met Ala Val Lys Ala Gln His His Thr Ser Glu Val Ser
  1               5                  10                  15

Asp Gln Arg Ile Arg Val Thr Ser Glu Val Leu Thr Cys Ile Lys Leu
             20                  25                  30

Ile Lys Met Tyr Thr Trp Glu Lys Pro Phe Ala Lys Ile Ile Glu Asp
         35                  40                  45

Leu Arg Arg Lys Glu Arg Lys Leu Leu Glu Lys Cys Gly Leu Val Gln
     50                  55                  60

Ser Leu Thr Ser Ile Thr Leu Phe Ile Ile Pro Thr Val Ala Thr Ala
 65                  70                  75                  80

Val Trp Val Leu Ile His Thr Ser Leu Lys Leu Lys Leu Thr Ala Ser
                 85                  90                  95

Met Ala Phe Ser Met Leu Ala Ser Leu Asn Leu Leu Arg Leu Ser Val
            100                 105                 110

Phe Phe Val Pro Ile Ala Val Lys Gly Leu Thr Asn Ser Lys Ser Ala
        115                 120                 125

Val Met Arg Phe Lys Lys Phe Phe Leu Gln Glu Ser Pro Val Phe Tyr
    130                 135                 140

Val Gln Thr Leu Gln Asp Pro Ser Lys Ala Leu Val Phe Glu Glu Ala
145                 150                 155                 160

Thr Leu Ser Trp Gln Gln Thr Cys Pro Gly Ile Val Asn Gly Ala Leu
                165                 170                 175

Glu Leu Glu Arg Asn Gly His Ala Ser Glu Gly Met Thr Arg Pro Arg
            180                 185                 190

Asp Ala Leu Gly Pro Glu Glu Glu Gly Asn Ser Leu Gly Pro Glu Leu
        195                 200                 205

His Lys Ile Asn Leu Val Val Ser Lys Gly Met Met Leu Gly Val Cys
    210                 215                 220

Gly Asn Thr Gly Ser Gly Lys Ser Ser Leu Leu Ser Ala Ile Leu Glu
225                 230                 235                 240

Glu Met His Leu Leu Glu Gly Ser Val Gly Val Gln Gly Ser Leu Ala
                245                 250                 255

Tyr Val Pro Gln Gln Ala Trp Ile Val Ser Gly Asn Ile Arg Glu Asn
            260                 265                 270

Ile Leu Met Gly Gly Ala Tyr Asp Lys Ala Arg Tyr Leu Gln Val Leu
        275                 280                 285
```

-continued

```
His Cys Cys Ser Leu Asn Arg Asp Leu Glu Leu Leu Pro Phe Gly Asp
    290                 295                 300

Met Thr Glu Ile Gly Glu Arg Gly Leu Asn Leu Ser Gly Gly Gln Lys
305                 310                 315                 320

Gln Arg Ile Ser Leu Ala Arg Ala Val Tyr Ser Asp Arg Gln Ile Tyr
                325                 330                 335

Leu Leu Asp Asp Pro Leu Ser Ala Val Asp Ala His Val Gly Lys His
            340                 345                 350

Ile Phe Glu Glu Cys Ile Lys Lys Thr Leu Arg Gly Lys Thr Val Val
        355                 360                 365

Leu Val Thr His Gln Leu Gln Tyr Leu Glu Phe Cys Gly Gln Ile Ile
    370                 375                 380

Leu Leu Glu Asn Gly Lys Ile Cys Glu Asn Gly Thr His Ser Glu Leu
385                 390                 395                 400

Met Gln Lys Lys Gly Lys Tyr Ala Gln Leu Ile Gln Lys Met His Lys
                405                 410                 415

Glu Ala Thr Ser Val Phe Arg Cys Pro Met Ser Phe Phe Asp Thr Ile
            420                 425                 430

Pro Ile Gly Arg Leu Leu Asn Cys Phe Ala Gly Asp Leu Glu Gln Leu
        435                 440                 445

Asp Gln Leu Leu Pro Ile Phe Ser Glu Gln Phe Leu Val Leu Ser Leu
    450                 455                 460

Met Val Ile Ala Val Leu Leu Ile Val Ser Val Leu Ser Pro Tyr Ile
465                 470                 475                 480

Leu Leu Met Gly Ala Ile Ile Met Val Ile Cys Phe Ile Tyr Tyr Met
                485                 490                 495

Met Phe Lys Lys Ala Ile Gly Val Phe Lys Arg Leu Glu Asn Tyr Ser
            500                 505                 510

Arg Ser Pro Leu Phe Ser His Ile Leu Asn Ser Leu Gln Gly Leu Ser
        515                 520                 525

Ser Ile His Val Tyr Gly Lys Thr Glu Asp Phe Ile Ser Gln Phe Lys
    530                 535                 540

Arg Leu Thr Asp Ala Gln Asn Asn Tyr Leu Leu Leu Phe Leu Ser Ser
545                 550                 555                 560

Thr Arg Trp Met Ala Leu Arg Leu Glu Ile Met Thr Asn Leu Val Thr
                565                 570                 575

Leu Ala Val Ala Leu Phe Val Ala Phe Gly Ile Ser Ser Thr Pro Tyr
            580                 585                 590

Ser Phe Lys Val Met Ala Val Asn Ile Val Leu Gln Leu Ala Ser Ser
        595                 600                 605

Phe Gln Ala Thr Ala Arg Ile Gly Leu Glu Thr Glu Ala Gln Phe Thr
    610                 615                 620

Ala Val Glu Arg Ile Leu Gln Tyr Met Lys Met Cys Val Ser Glu Ala
625                 630                 635                 640

Pro Leu His Met Glu Gly Thr Ser Cys Pro Gln Gly Trp Pro Gln His
                645                 650                 655

Gly Glu Ile Ile Phe Gln Asp Tyr His Met Lys Tyr Arg Asp Asn Thr
            660                 665                 670

Pro Thr Val Leu His Gly Ile Asn Leu Thr Ile Arg Gly His Glu Val
        675                 680                 685

Val Gly Ile Val Gly Arg Thr Gly Ser Gly Lys Ser Ser Leu Gly Met
    690                 695                 700

Ala Leu Phe Arg Leu Val Glu Pro Met Ala Gly Arg Ile Leu Ile Asp
```

```
                705                 710                 715                 720
        Gly Val Asp Ile Cys Ser Ile Gly Leu Glu Asp Leu Arg Ser Lys Leu
                        725                 730                 735

Ser Val Ile Pro Gln Asp Pro Val Leu Leu Ser Gly Thr Ile Arg Phe
                        740                 745                 750

Asn Leu Asp Pro Phe Asp Arg His Thr Asp Gln Gln Ile Trp Asp Ala
                        755                 760                 765

Leu Glu Arg Thr Phe Leu Thr Lys Ala Ile Ser Lys Phe Pro Lys Lys
                        770                 775                 780

Leu His Thr Asp Val Val Glu Asn Gly Asn Phe Ser Val Gly Glu
        785                 790                 795                 800

Arg Gln Leu Leu Cys Ile Ala Arg Ala Val Leu Arg Asn Ser Lys Ile
                        805                 810                 815

Ile Leu Ile Asp Glu Ala Thr Ala Ser Ile Asp Met Glu Thr Asp Thr
                        820                 825                 830

Leu Ile Gln Arg Thr Ile Arg Glu Ala Phe Gln Gly Cys Thr Val Leu
                        835                 840                 845

Val Ile Ala His Arg Val Thr Thr Val Leu Asn Cys Asp His Ile Leu
        850                 855                 860

Val Met Gly Asn Gly Lys Val Val Glu Phe Asp Arg Pro Glu Val Leu
        865                 870                 875                 880

Arg Lys Lys Pro Gly Ser Leu Phe Ala Ala Leu Met Ala Thr Ala Thr
                        885                 890                 895

Ser Ser Leu Arg
                900

<210> SEQ ID NO 13
<211> LENGTH: 2937
<212> TYPE: DNA
<213> ORGANISM: homo sapiens

<400> SEQUENCE: 13
atgactagga agaggacata ctgggtgccc aactcttctg gtggcctcgt gaatcgtggc         60
atcgacatag gcgatgacat ggtttcagga cttatttata aaacctatac tctccaagat        120
ggcccctgga gtcagcaaga gagaaatcct gaggctccag ggagggcagc tgtcccaccg        180
tgggggaagt atgatgctgc cttgagaacc atgattccct tccgtcccaa gccgaggttt        240
cctgcccccc agcccctgga caatgctggc ctgttctcct acctcaccgt gtcatggctc        300
accccgctca tgatccaaag cttacggagt cgcttagatg agaacaccat ccctccactg        360
tcagtccatg atgcctcaga caaaaatgtc caaaggcttc accgcctttg ggaagaagaa        420
gtctcaaggc gagggattga aaaagcttca gtgcttctgg tgatgctgag gttccagaga        480
acaaggttga ttttcgatgc acttctgggc atctgcttct gcattgccag tgtactcggg        540
ccaatattga ttataccaaa gatcctggaa tattcagaag agcagttggg gaatgttgtc        600
catggagtgg gactctgctt tgcccttttt ctctccgaat gtgtgaagtc tctgagtttc        660
tcctccagtt ggatcatcaa ccaacgcaca gccatcaggt tccaagcagc tgtttcctcc        720
tttgcctttg agaagctcat ccaatttaag tctgtaatac acatcacctc aggagaggcc        780
atcagcttct tcaccggtga tgtaaactac ctgtttgaag gggtgtgcta tggccccta         840
gtactgatca cctgcgcatc gctggtcatc tgcagcattt cttcctactt cattattgga        900
tacactgcat ttattgccat cttatgctat ctcctggttt tcccactgga ggtattcatg        960
acaagaatgg ctgtgaaggc tcagcatcac acatctgagg tcagcgacca gcgcatccgt       1020
```

-continued

```
gtgaccagtg aagttctcac ttgcattaag ctgattaaaa tgtacacatg ggagaaacca    1080
tttgcaaaaa tcattgaaga cctaagaagg aaggaaagga agctattgga gaagtgcggg    1140
cttgtccaga gcctgacaag tataaccttg ttcatcatcc ccacagtggc cacagcggtc    1200
tgggttctca tccacacatc cttaaagctg aaactcacag cgtcaatggc cttcagcatg    1260
ctggcctcct tgaatctcct tcggctgtca gtgttctttg tgcctattgc agtcaaaggt    1320
ctcacgaatt ccaagtctgc agtgatgagg ttcaagaagt ttttcctcca ggagagccct    1380
gttttctatg tccagacatt acaagacccc agcaaagctc tggtctttga ggaggccacc    1440
ttgtcatggc aacagacctg tcccgggatc gtcaatgggg cactggagct ggagaggaac    1500
gggcatgctt ctgagggggat gaccaggcct agagatgccc tcgggccaga ggaagaaggg    1560
aacagcctgg gcccagagtt gcacaagatc aacctggtgg tgtccaaggg gatgatgtta    1620
ggggtctgcg gcaacacggg gagtggtaag agcagcctgt tgtcagccat cctggaggag    1680
atgcacttgc tcgagggctc ggtggggggtg cagggaagcc tggcctatgt cccccagcag    1740
gcctggatcg tcagcgggaa catcaggagg aacatcctca tgggaggcgc atatgacaag    1800
gcccgatacc tccaggtgct ccactgctgc tccctgaatc gggacctgga acttctgccc    1860
tttggagaca tgacagagat tggagagcgg ggcctcaacc tctctggggg gcagaaacag    1920
aggatcagcc tggcccgcgc cgtctattcc gaccgtcaga tctacctgct ggacgacccc    1980
ctgtctgctg tggacgccca cgtggggaag cacattttttg aggagtgcat taagaagaca    2040
ctcagggggga agacggtcgt cctggtgacc caccagctgc agtacttaga attttgtggc    2100
cagatcattt tgttggaaaa tgggaaaatc tgtgaaaatg gaactcacag tgagttaatg    2160
cagaaaaagg ggaaatatgc ccaacttatc cagaagatgc acaaggaagc cacttcggac    2220
atgttgcagg acacagcaaa gatagcagag aagccaaagg tagaaagtca ggctctggcc    2280
acctccctgg aagagtctct caacggaaat gctgtgccgg agcatcagct cacacaggag    2340
gaggagatgg aagaaggctc cttgagttgg agggtctacc accactacat ccaggcagct    2400
ggaggttaca tggtctcttg cataattttc ttcttcgtgg tgctgatcgt cttcttaacg    2460
atcttcagct tctggtggct gagctactgg ttggagcagg gctcggggac caatagcagc    2520
cgagagagca atggaaccat ggcagacctg gcaacattg cagacaatcc tcaactgtcc    2580
ttctaccagc tggtgtacgg gctcaacgcc ctgctcctca tctgtgtggg ggtctgctcc    2640
tcagggattt tcaccaaggt cacgaggaag gcatccacgg ccctgcacaa caagctcttc    2700
aacaaggttt tccgctgccc catgagtttc tttgacacca tcccaatagg ccggcttttg    2760
aactgcttcg cagggactt ggaacagctg gaccagctct tgcccatctt ttcagagcag    2820
ttcctggtcc tgtccttaat ggtgatcgcc gtcctgttga ttgtcagtgt gctgtctcca    2880
tatatcctgt taatgggagc cataatcatg gttatttgct tcatttatta tatgtga      2937
```

<210> SEQ ID NO 14
<211> LENGTH: 975
<212> TYPE: PRT
<213> ORGANISM: homo sapiens

<400> SEQUENCE: 14

Met Thr Arg Lys Arg Thr Tyr Trp Val Pro Asn Ser Ser Gly Gly Leu
1               5                   10                  15

Val Asn Arg Gly Ile Asp Ile Gly Asp Asp Met Val Ser Gly Leu Ile
            20                  25                  30

```
Tyr Lys Thr Tyr Thr Leu Gln Asp Gly Pro Trp Ser Gln Glu Arg
        35                  40                  45

Asn Pro Glu Ala Pro Gly Arg Ala Val Pro Pro Trp Gly Lys Tyr
    50                  55                  60

Asp Ala Ala Leu Arg Thr Met Ile Pro Phe Arg Pro Lys Pro Arg Phe
65                  70                  75                  80

Pro Ala Pro Gln Pro Leu Gly Leu Phe Ser Tyr Leu Thr Val Ser Trp
                85                  90                  95

Leu Thr Pro Leu Met Ile Gln Ser Leu Arg Ser Arg Leu Asp Glu Asn
                100                 105                 110

Thr Ile Pro Pro Leu Ser Val His Asp Ala Ser Asp Lys Asn Val Gln
                115                 120                 125

Arg Leu His Arg Leu Trp Glu Glu Val Ser Arg Arg Gly Ile Glu
    130                 135                 140

Lys Ala Ser Val Leu Leu Val Met Leu Arg Phe Gln Arg Thr Arg Leu
145                 150                 155                 160

Ile Phe Asp Ala Leu Leu Gly Ile Cys Phe Cys Ile Ala Ser Val Leu
                165                 170                 175

Gly Pro Ile Leu Ile Pro Lys Ile Leu Glu Tyr Ser Glu Glu Gln
                180                 185                 190

Leu Gly Asn Val Val His Gly Val Gly Leu Cys Phe Ala Leu Phe Leu
                195                 200                 205

Ser Glu Cys Val Lys Ser Leu Ser Phe Ser Ser Ser Trp Ile Ile Asn
    210                 215                 220

Gln Arg Thr Ala Ile Arg Phe Gln Ala Ala Val Ser Ser Phe Ala Phe
225                 230                 235                 240

Glu Lys Leu Ile Gln Phe Lys Ser Val Ile His Ile Thr Ser Gly Glu
                245                 250                 255

Ala Ile Ser Phe Phe Thr Gly Asp Val Asn Tyr Leu Phe Glu Gly Val
                260                 265                 270

Cys Tyr Gly Pro Leu Val Leu Ile Thr Cys Ala Ser Leu Val Ile Cys
    275                 280                 285

Ser Ile Ser Ser Tyr Phe Ile Ile Gly Tyr Thr Ala Phe Ile Ala Ile
    290                 295                 300

Leu Cys Tyr Leu Leu Val Phe Pro Leu Glu Val Phe Met Thr Arg Met
305                 310                 315                 320

Ala Val Lys Ala Gln His His Thr Ser Glu Val Ser Asp Gln Arg Ile
                325                 330                 335

Arg Val Thr Ser Glu Val Leu Thr Cys Ile Lys Leu Ile Lys Met Tyr
                340                 345                 350

Thr Trp Glu Lys Pro Phe Ala Lys Ile Ile Glu Asp Leu Arg Arg Lys
                355                 360                 365

Glu Arg Lys Leu Leu Glu Lys Cys Gly Leu Val Gln Ser Leu Thr Ser
    370                 375                 380

Ile Thr Leu Phe Ile Ile Pro Thr Val Ala Thr Ala Val Trp Val Leu
385                 390                 395                 400

Ile His Thr Ser Leu Lys Leu Lys Leu Thr Ala Ser Met Ala Phe Ser
                405                 410                 415

Met Leu Ala Ser Leu Asn Leu Leu Arg Leu Ser Val Phe Phe Val Pro
                420                 425                 430

Ile Ala Val Lys Gly Leu Thr Asn Ser Lys Ser Ala Val Met Arg Phe
                435                 440                 445

Lys Lys Phe Phe Leu Gln Glu Ser Pro Val Phe Tyr Val Gln Thr Leu
```

-continued

```
                450                 455                 460
Gln Asp Pro Ser Lys Ala Leu Val Phe Glu Ala Thr Leu Ser Trp
465                 470                 475                 480

Gln Gln Thr Cys Pro Gly Ile Val Asn Gly Ala Leu Glu Leu Arg
                485                 490                 495

Asn Gly His Ala Ser Glu Gly Met Thr Arg Pro Arg Asp Ala Leu Gly
                500                 505                 510

Pro Glu Glu Glu Gly Asn Ser Leu Gly Pro Glu Leu His Lys Ile Asn
            515                 520                 525

Leu Val Val Ser Lys Gly Met Met Leu Gly Val Cys Gly Asn Thr Gly
530                 535                 540

Ser Gly Lys Ser Ser Leu Leu Ser Ala Ile Leu Glu Glu Met His Leu
545                 550                 555                 560

Leu Glu Gly Ser Val Gly Val Gln Gly Ser Leu Ala Tyr Val Pro Gln
                565                 570                 575

Gln Ala Trp Ile Val Ser Gly Asn Ile Arg Glu Asn Ile Leu Met Gly
                580                 585                 590

Gly Ala Tyr Asp Lys Ala Arg Tyr Leu Gln Val Leu His Cys Cys Ser
                595                 600                 605

Leu Asn Arg Asp Leu Glu Leu Leu Pro Phe Gly Asp Met Thr Glu Ile
                610                 615                 620

Gly Glu Arg Gly Leu Asn Leu Ser Gly Gly Gln Lys Gln Arg Ile Ser
625                 630                 635                 640

Leu Ala Arg Ala Val Tyr Ser Asp Arg Gln Ile Tyr Leu Leu Asp Asp
                645                 650                 655

Pro Leu Ser Ala Val Asp Ala His Val Gly Lys His Ile Phe Glu Glu
                660                 665                 670

Cys Ile Lys Lys Thr Leu Arg Gly Lys Thr Val Val Leu Val Thr His
                675                 680                 685

Gln Leu Gln Tyr Leu Glu Phe Cys Gly Gln Ile Ile Leu Leu Glu Asn
                690                 695                 700

Gly Lys Ile Cys Glu Asn Gly Thr His Ser Glu Leu Met Gln Lys Lys
705                 710                 715                 720

Gly Lys Tyr Ala Gln Leu Ile Gln Lys Met His Lys Glu Ala Thr Ser
                725                 730                 735

Asp Met Leu Gln Asp Thr Ala Lys Ile Ala Glu Lys Pro Lys Val Glu
                740                 745                 750

Ser Gln Ala Leu Ala Thr Ser Leu Glu Glu Ser Leu Asn Gly Asn Ala
                755                 760                 765

Val Pro Glu His Gln Leu Thr Gln Glu Glu Met Glu Glu Gly Ser
770                 775                 780

Leu Ser Trp Arg Val Tyr His His Tyr Ile Gln Ala Ala Gly Gly Tyr
785                 790                 795                 800

Met Val Ser Cys Ile Ile Phe Phe Phe Val Val Leu Ile Val Phe Leu
                805                 810                 815

Thr Ile Phe Ser Phe Trp Trp Leu Ser Tyr Trp Leu Glu Gln Gly Ser
                820                 825                 830

Gly Thr Asn Ser Ser Arg Glu Ser Asn Gly Thr Met Ala Asp Leu Gly
                835                 840                 845

Asn Ile Ala Asp Asn Pro Gln Leu Ser Phe Tyr Gln Leu Val Tyr Gly
850                 855                 860

Leu Asn Ala Leu Leu Leu Ile Cys Val Gly Val Cys Ser Ser Gly Ile
865                 870                 875                 880
```

Phe Thr Lys Val Thr Arg Lys Ala Ser Thr Ala Leu His Asn Lys Leu
                885                 890                 895

Phe Asn Lys Val Phe Arg Cys Pro Met Ser Phe Phe Asp Thr Ile Pro
            900                 905                 910

Ile Gly Arg Leu Leu Asn Cys Phe Ala Gly Asp Leu Glu Gln Leu Asp
        915                 920                 925

Gln Leu Leu Pro Ile Phe Ser Glu Gln Phe Leu Val Leu Ser Leu Met
    930                 935                 940

Val Ile Ala Val Leu Leu Ile Val Ser Val Leu Ser Pro Tyr Ile Leu
945                 950                 955                 960

Leu Met Gly Ala Ile Ile Met Val Ile Cys Phe Ile Tyr Tyr Met
                965                 970                 975

<210> SEQ ID NO 15
<211> LENGTH: 3075
<212> TYPE: DNA
<213> ORGANISM: homo sapiens

<400> SEQUENCE: 15
atgactagga agaggacata ctgggtgccc aactcttctg gtggcctcgt gaatcgtggc      60
atcgacatag gcgatgacat ggtttcagga cttatttata aaacctatac tctccaagat     120
ggcccctgga gtcagcaaga gagaaatcct gaggctccag ggagggcagc tgtcccaccg     180
tgggggaagt atgatgctgc cttgagaacc atgattccct tccgtcccaa gccgaggttt     240 cctgccccc agcccctgga caatgctggc ctgttctcct acctcaccgt gtcatggctc     300
accccgctca tgatccaaag cttacggagt cgcttagatg agaacaccat ccctccactg     360
tcagtccatg atgcctcaga caaaaatgtc caaaggcttc accgcctttg ggaagaagaa     420
gtctcaaggc gagggattga aaaagcttca gtgcttctgg tgatgctgag gttccagaga     480
acaaggttga ttttcgatgc acttctgggc atctgcttct gcattgccag tgtactcggg     540
ccaatattga ttataccaaa gatcctggaa tattcagaag agcagttggg gaatgttgtc     600
catggagtgg gactctgctt tgcccttttt ctctccgaat gtgtgaagtc tctgagtttc     660
tcctccagtt ggatcatcaa ccaacgcaca gccatcaggt tccaagcagc tgtttcctcc     720
tttgcctttg agaagctcat ccaatttaag tctgtaatac acatcacctc aggagaggcc     780
atcagcttct tcaccggtga tgtaaactac ctgtttgaag gggtgtgcta tggaccccta     840
gtactgatca cctgcgcatc gctggtcatc tgcagcattt cttcctactt cattattgga     900
tacactgcat ttattgccat cttatgctat ctcctggttt tcccactgga ggtattcatg     960
acaagaatgg ctgtgaaggc tcagcatcac acatctgagg tcagcgacca gcgcatccgt    1020
gtgaccagtg aagttctcac ttgcattaag ctgattaaaa tgtacacatg ggagaaacca    1080
tttgcaaaaa tcattgaaga cctaagaagg aaggaaagga agctattgga agtgcggg     1140 cttgtccaga gcctgacaag tataaccttg ttcatcatcc ccacagtggc cacagcggtc    1200
tgggttctca tccacacatc cttaaagctg aaactcacag cgtcaatggc cttcagcatg    1260
ctggcctcct tgaatctcct tcggctgtca gtgttctttg tgcctattgc agtcaaaggt    1320
ctcacgaatt ccagtctgc agtgatgagg ttcaagaagt ttttcctcca ggagagccct    1380
gttttctatg tccagacatt acaagacccc agcaaagctc tggtctttga ggaggccacc    1440
ttgtcatggc aacagacctg tcccgggatc gtcaatgggg cactggagct ggagaggaac    1500
gggcatgctt ctgaggggat gaccaggcct agagatgccc tcgggccaga ggaagaaggg    1560

-continued

```
aacagcctgg gcccagagtt gcacaagatc aacctggtgg tgtccaaggg gatgatgtta    1620
ggggtctgcg gcaacacggg gagtggtaag agcagcctgt tgtcagccat cctggaggag    1680
atgcacttgc tcgagggctc ggtggggtg cagggaagcc tggcctatgt cccccagcag    1740
gcctggatcg tcagcgggaa catcaggag aacatcctca tgggaggcgc atatgacaag    1800
gcccgatacc tccaggtgct ccactgctgc tccctgaatc gggacctgga acttctgccc    1860
tttggagaca tgacagagat tggagagcgg ggcctcaacc tctctggggg gcagaaacag    1920
aggatcagcc tggcccgcgc cgtctattcc gaccgtcaga tctacctgct ggacgacccc    1980
ctgtctgctg tggacgccca cgtggggaag cacattttg aggagtgcat taagaagaca    2040
ctcaggggga agacggtcgt cctggtgacc caccagctgc agtacttaga attttgtggc    2100
cagatcattt tgttggaaaa tgggaaaatc tgtgaaaatg gaactcacag tgagttaatg    2160
cagaaaaagg ggaaatatgc ccaacttatc cagaagatgc acaaggaagc cacttcggac    2220
atgttgcagg acacagcaaa gatagcagag aagccaaagg tagaaagtca ggctctggcc    2280
acctccctgg aagagtctct caacggaaat gctgtgccgg agcatcagct cacacaggag    2340
gaggagatga agaaggctc cttgagttgg agggtctacc accactacat ccaggcagct    2400
ggaggttaca tggtctcttg cataattttc ttcttcgtgg tgctgatcgt cttcttaacg    2460
atcttcagct tctggtggct gagctactgg ttggagcagg gctcggggac caatagcagc    2520
cgagagagca atggaaccat ggcagacctg ggcaacattg cagacaatcc tcaactgtcc    2580
ttctaccagc tggtgtacgg gctcaacgcc ctgctcctca tctgtgtggg ggtctgctcc    2640
tcagggattt tcaccaaggt cacgaggaag gcatccacgg ccctgcacaa caagctcttc    2700
aacaaggttt tccgctgccc catgagtttc tttgacacca tcccaatagg ccggcttttg    2760
aactgcttcg caggggactt ggaacagctg gaccagctct gcccatctt ttcagagcag    2820 ttcctggtcc tgtccttaat ggtgatcgcc gtcctgttga ttgtcagtgt gctgtctcca    2880
tatatcctgt taatgggagc cataatcatg gttatttgct tcatttatta tatgatgttc    2940
aagaaggcca tcggtgtgtt caagagactg gagaactata gccggtctcc tttattctcc    3000
cacatcctca attctctgca aggcctgagc tccatccatg tctatggaaa aactgaagac    3060
ttcatcagcc agtga                                                     3075
```

<210> SEQ ID NO 16
<211> LENGTH: 1021
<212> TYPE: PRT
<213> ORGANISM: homo sapiens

<400> SEQUENCE: 16

```
Met Thr Arg Lys Arg Thr Tyr Trp Val Pro Asn Ser Ser Gly Gly Leu
 1               5                  10                  15

Val Asn Arg Gly Ile Asp Ile Gly Asp Asp Met Val Ser Gly Leu Ile
             20                  25                  30

Tyr Lys Thr Tyr Thr Leu Gln Asp Gly Pro Trp Ser Gln Gln Glu Arg
         35                  40                  45

Asn Pro Glu Ala Pro Gly Arg Ala Ala Val Pro Trp Gly Lys Tyr
     50                  55                  60

Asp Ala Ala Leu Arg Thr Met Ile Pro Phe Arg Pro Lys Pro Arg Phe
 65                  70                  75                  80

Pro Ala Pro Gln Pro Leu Gly Leu Phe Ser Tyr Leu Thr Val Ser Trp
                 85                  90                  95

Leu Thr Pro Leu Met Ile Gln Ser Leu Arg Ser Arg Leu Asp Glu Asn
```

-continued

```
                100                 105                 110
Thr Ile Pro Pro Leu Ser Val His Asp Ala Ser Asp Lys Asn Val Gln
            115                 120                 125
Arg Leu His Arg Leu Trp Glu Glu Val Ser Arg Arg Gly Ile Glu
        130                 135                 140
Lys Ala Ser Val Leu Leu Val Met Leu Arg Phe Gln Arg Thr Arg Leu
145                 150                 155                 160
Ile Phe Asp Ala Leu Leu Gly Ile Cys Phe Cys Ile Ala Ser Val Leu
                165                 170                 175
Gly Pro Ile Leu Ile Pro Lys Ile Leu Glu Tyr Ser Glu Glu Gln
            180                 185                 190
Leu Gly Asn Val Val His Gly Val Gly Leu Cys Phe Ala Leu Phe Leu
        195                 200                 205
Ser Glu Cys Val Lys Ser Leu Ser Phe Ser Ser Ser Trp Ile Ile Asn
    210                 215                 220
Gln Arg Thr Ala Ile Arg Phe Gln Ala Ala Val Ser Ser Phe Ala Phe
225                 230                 235                 240
Glu Lys Leu Ile Gln Phe Lys Ser Val Ile His Ile Thr Ser Gly Glu
                245                 250                 255
Ala Ile Ser Phe Phe Thr Gly Asp Val Asn Tyr Leu Phe Glu Gly Val
            260                 265                 270
Cys Tyr Gly Pro Leu Val Leu Ile Thr Cys Ala Ser Leu Val Ile Cys
        275                 280                 285
Ser Ile Ser Ser Tyr Phe Ile Ile Gly Tyr Thr Ala Phe Ile Ala Ile
    290                 295                 300
Leu Cys Tyr Leu Leu Val Phe Pro Leu Glu Val Phe Met Thr Arg Met
305                 310                 315                 320
Ala Val Lys Ala Gln His His Thr Ser Glu Val Ser Asp Gln Arg Ile
                325                 330                 335
Arg Val Thr Ser Glu Val Leu Thr Cys Ile Lys Leu Ile Lys Met Tyr
            340                 345                 350
Thr Trp Glu Lys Pro Phe Ala Lys Ile Ile Glu Asp Leu Arg Arg Lys
        355                 360                 365
Glu Arg Lys Leu Leu Glu Lys Cys Gly Leu Val Gln Ser Leu Thr Ser
    370                 375                 380
Ile Thr Leu Phe Ile Ile Pro Thr Val Ala Thr Ala Val Trp Val Leu
385                 390                 395                 400
Ile His Thr Ser Leu Lys Leu Lys Leu Thr Ala Ser Met Ala Phe Ser
                405                 410                 415
Met Leu Ala Ser Leu Asn Leu Leu Arg Leu Ser Val Phe Phe Val Pro
            420                 425                 430
Ile Ala Val Lys Gly Leu Thr Asn Ser Lys Ser Ala Val Met Arg Phe
        435                 440                 445
Lys Lys Phe Phe Leu Gln Glu Ser Pro Val Phe Tyr Val Gln Thr Leu
    450                 455                 460
Gln Asp Pro Ser Lys Ala Leu Val Phe Glu Glu Ala Thr Leu Ser Trp
465                 470                 475                 480
Gln Gln Thr Cys Pro Gly Ile Val Asn Gly Ala Leu Glu Leu Glu Arg
                485                 490                 495
Asn Gly His Ala Ser Glu Gly Met Thr Arg Pro Arg Asp Ala Leu Gly
            500                 505                 510
Pro Glu Glu Glu Gly Asn Ser Leu Gly Pro Glu Leu His Lys Ile Asn
        515                 520                 525
```

-continued

```
Leu Val Val Ser Lys Gly Met Met Leu Gly Val Cys Gly Asn Thr Gly
    530                 535                 540
Ser Gly Lys Ser Ser Leu Leu Ser Ala Ile Leu Glu Glu Met His Leu
545                 550                 555                 560
Leu Glu Gly Ser Val Gly Val Gln Gly Ser Leu Ala Tyr Val Pro Gln
                565                 570                 575
Gln Ala Trp Ile Val Ser Gly Asn Ile Arg Glu Asn Ile Leu Met Gly
            580                 585                 590
Gly Ala Tyr Asp Lys Ala Arg Tyr Leu Gln Val Leu His Cys Cys Ser
        595                 600                 605
Leu Asn Arg Asp Leu Glu Leu Leu Pro Phe Gly Asp Met Thr Glu Ile
    610                 615                 620
Gly Glu Arg Gly Leu Asn Leu Ser Gly Gly Gln Lys Gln Arg Ile Ser
625                 630                 635                 640
Leu Ala Arg Ala Val Tyr Ser Asp Arg Gln Ile Tyr Leu Leu Asp Asp
                645                 650                 655
Pro Leu Ser Ala Val Asp Ala His Val Gly Lys His Ile Phe Glu Glu
            660                 665                 670
Cys Ile Lys Lys Thr Leu Arg Gly Lys Thr Val Val Leu Val Thr His
        675                 680                 685
Gln Leu Gln Tyr Leu Glu Phe Cys Gly Gln Ile Ile Leu Leu Glu Asn
    690                 695                 700
Gly Lys Ile Cys Glu Asn Gly Thr His Ser Glu Leu Met Gln Lys Lys
705                 710                 715                 720
Gly Lys Tyr Ala Gln Leu Ile Gln Lys Met His Lys Glu Ala Thr Ser
                725                 730                 735
Asp Met Leu Gln Asp Thr Ala Lys Ile Ala Glu Lys Pro Lys Val Glu
            740                 745                 750
Ser Gln Ala Leu Ala Thr Ser Leu Glu Glu Ser Leu Asn Gly Asn Ala
        755                 760                 765
Val Pro Glu His Gln Leu Thr Gln Glu Glu Met Glu Glu Gly Ser
    770                 775                 780
Leu Ser Trp Arg Val Tyr His His Tyr Ile Gln Ala Ala Gly Gly Tyr
785                 790                 795                 800
Met Val Ser Cys Ile Ile Phe Phe Val Val Leu Ile Val Phe Leu
                805                 810                 815
Thr Ile Phe Ser Phe Trp Trp Leu Ser Tyr Trp Leu Glu Gln Gly Ser
            820                 825                 830
Gly Thr Asn Ser Ser Arg Glu Ser Asn Gly Thr Met Ala Asp Leu Gly
        835                 840                 845
Asn Ile Ala Asp Asn Pro Gln Leu Ser Phe Tyr Gln Leu Val Tyr Gly
    850                 855                 860
Leu Asn Ala Leu Leu Leu Ile Cys Val Gly Val Cys Ser Ser Gly Ile
865                 870                 875                 880
Phe Thr Lys Val Thr Arg Lys Ala Ser Thr Ala Leu His Asn Lys Leu
                885                 890                 895
Phe Asn Lys Val Phe Arg Cys Pro Met Ser Phe Phe Asp Thr Ile Pro
            900                 905                 910
Ile Gly Arg Leu Leu Asn Cys Phe Ala Gly Asp Leu Glu Gln Leu Asp
        915                 920                 925
Gln Leu Leu Pro Ile Phe Ser Glu Gln Phe Leu Val Leu Ser Leu Met
    930                 935                 940
```

```
Val Ile Ala Val Leu Leu Ile Val Ser Val Leu Ser Pro Tyr Ile Leu
945                 950                 955                 960

Leu Met Gly Ala Ile Ile Met Val Ile Cys Phe Ile Tyr Tyr Met Met
            965                 970                 975

Phe Lys Lys Ala Ile Gly Val Phe Lys Arg Leu Glu Asn Tyr Ser Arg
        980                 985                 990

Ser Pro Leu Phe Ser His Ile Leu Asn Ser Leu Gln Gly Leu Ser Ser
        995                 1000                1005

Ile His Val Tyr Gly Lys Thr Glu Asp Phe Ile Ser Gln
    1010                1015                1020

<210> SEQ ID NO 17
<211> LENGTH: 4149
<212> TYPE: DNA
<213> ORGANISM: homo sapiens

<400> SEQUENCE: 17
```

| | | | | | | |
|---|---|---|---|---|---|---|
| atgactagga | agaggacata | ctgggtgccc | aactcttctg | gtggcctcgt | gaatcgtggc | 60 |
| atcgacatag | gcgatgacat | ggtttcagga | cttatttata | aaacctatac | tctccaagat | 120 |
| ggcccctgga | gtcagcaaga | gagaaatcct | gaggctccag | ggagggcagc | tgtcccaccg | 180 |
| tgggggaagt | atgatgctgc | cttgagaacc | atgattccct | tccgtcccaa | gccgaggttt | 240 |
| cctgcccccc | agcccctgga | caatgctggc | ctgttctcct | acctcaccgt | gtcatggctc | 300 |
| accccgctca | tgatccaaag | cttacggagt | cgcttagatg | agaacaccat | ccctccactg | 360 |
| tcagtccatg | atgcctcaga | caaaaatgtc | caaaggcttc | accgcctttg | ggaagaagaa | 420 |
| gtctcaaggc | gagggattga | aaaagcttca | gtgcttctgg | tgatgctgag | gttccagaga | 480 |
| acaaggttga | ttttcgatgc | acttctgggc | atctgcttct | gcattgccag | tgtactcggg | 540 |
| ccaatattga | ttataccaaa | gatcctggaa | tattcagaag | agcagttggg | gaatgttgtc | 600 |
| catggagtgg | gactctgctt | tgccctttt | ctctccgaat | gtgtgaagtc | tctgagtttc | 660 |
| tcctccagtt | ggatcatcaa | ccaacgcaca | gccatcaggt | tccaagcagc | tgtttcctcc | 720 |
| tttgcctttg | agaagctcat | ccaatttaag | tctgtaatac | acatcacctc | aggagaggcc | 780 |
| atcagcttct | tcaccggtga | tgtaaactac | ctgtttgaag | gggtgtgcta | tggaccccta | 840 |
| gtactgatca | cctgcgcatc | gctggtcatc | tgcagcattt | cttcctactt | cattattgga | 900 |
| tacactgcat | ttattgccat | cttatgctat | ctcctggttt | tcccactgga | ggtattcatg | 960 |
| acaagaatgg | ctgtgaaggc | tcagcatcac | acatctgagg | tcagcgacca | gcgcatccgt | 1020 |
| gtgaccagtg | aagttctcac | ttgcattaag | ctgattaaaa | tgtacacatg | ggagaaacca | 1080 |
| tttgcaaaaa | tcattgaaga | cctaagaagg | aaggaaagga | agctattgga | gaagtgcggg | 1140 |
| cttgtccaga | gcctgacaag | tataaccttg | ttcatcatcc | ccacagtggc | cacagcggtc | 1200 |
| tgggttctca | tccacacatc | cttaaagctg | aaactcacag | cgtcaatggc | cttcagcatg | 1260 |
| ctggcctcct | tgaatctcct | tcggctgtca | gtgttctttg | tgcctattgc | agtcaaaggt | 1320 |
| ctcacgaatt | ccaagtctgc | agtgatgagg | ttcaagaagt | ttttcctcca | ggagagccct | 1380 |
| gttttctatg | tccagacatt | acaagacccc | agcaaagctc | tggtctttga | ggaggccacc | 1440 |
| ttgtcatggc | aacagacctg | tccgggatc | gtcaatgggg | cactggagct | ggagaggaac | 1500 |
| gggcatgctt | ctgaggggat | gaccaggcct | agagatgccc | tcgggccaga | ggaagaaggg | 1560 |
| aacagcctgg | gcccagagtt | gcacaagatc | aacctggtgg | tgtccaaggg | gatgatgtta | 1620 |
| ggggtctgcg | gcaacacggg | gagtggtaag | agcagcctgt | tgtcagccat | cctggaggag | 1680 |

```
atgcacttgc tcgagggctc ggtgggggtg cagggaagcc tggcctatgt cccccagcag   1740
gcctggatcg tcagcgggaa catcaggag aacatcctca tgggaggcgc atatgacaag    1800
gcccgatacc tccaggtgct ccactgctgc tccctgaatc gggacctgga acttctgccc   1860
tttggagaca tgacagagat tggagagcgg ggcctcaacc tctctggggg gcagaaacag   1920
aggatcagcc tggcccgcgc cgtctattcc gaccgtcaga tctacctgct ggacgacccc   1980
ctgtctgctg tggacgccca cgtggggaag cacattttg aggagtgcat taagaagaca    2040
ctcaggggga agacggtcgt cctggtgacc caccagctgc agtacttaga attttgtggc   2100
cagatcattt tgttggaaaa tgggaaaatc tgtgaaaatg gaactcacag tgagttaatg   2160
cagaaaaagg ggaaatatgc ccaacttatc agaagatgc acaaggaagc cacttcggac    2220
atgttgcagg acacagcaaa gatagcagag aagccaaagg tagaaagtca ggctctggcc   2280
acctccctgg aagagtctct caacggaaat gctgtgccgg agcatcagct cacacaggag   2340
gaggagatgg aagaaggctc cttgagttgg agggtctacc accactacat ccaggcagct   2400
ggaggttaca tggtctcttg cataattttc ttcttcgtgg tgctgatcgt cttcttaacg   2460
atcttcagct tctggtggct gagctactgg ttggagcagg gctcggggac caatagcagc   2520
cgagagagca atggaaccat ggcagacctg gcaacattg cagacaatcc tcaactgtcc    2580
ttctaccagc tggtgtacgg gctcaacgcc ctgctcctca tctgtgtggg ggtctgctcc   2640
tcagggattt tcaccaaggt cacgaggaag gcatccacgg ccctgcacaa caagctcttc   2700
aacaaggttt tccgctgccc catgagtttc tttgacacca tcccaatagg ccggcttttg   2760
aactgcttcg caggggactt ggaacagctg gaccagctct gcccatctt ttcagagcag    2820 ttcctggtcc tgtccttaat ggtgatcgcc gtcctgttga ttgtcagtgt gctgtctcca   2880
tatatcctgt taatgggagc cataatcatg gttatttgct tcatttatta tatgatgttc   2940
aagaaggcca tcggtgtgtt caagagactg gagaactata gccggtctcc tttattctcc   3000
cacatcctca attctctgca aggcctgagc tccatccatg tctatggaaa aactgaagac   3060
ttcatcagcc agtttaagag gctgactgat gcgcagaata actacctgct gttgtttcta   3120
tcttccacac gatggatggc attgaggctg agatcatga ccaaccttgt gaccttggct    3180
gttgccctgt tcgtggcttt tggcatttcc tccacccct actccttaa agtcatggct    3240 gtcaacatcg tgctgcagct ggcgtccagc ttccaggcca ctgcccggat tggcttggag   3300
acagaggcac agttcacggc tgtagagagg atactgcagt acatgaagat gtgtgtctcg   3360
gaagctcctt tacacatgga aggcacaagt tgtccccagg ggtggccaca gcatgggaa    3420 atcatatttc aggattatca catgaaatac agagacaaca cacccaccgt gcttcacggc   3480
atcaacctga ccatccgcgg ccacgaagtg gtgggcatcg tgggaaggac gggctctggg   3540
aagtcctcct tgggcatggc tctcttccgc ctggtggagc ccatggcagg ccggattctc   3600
attgacggcg tggacatttg cagcatcggc ctggaggact tgcggtccaa gctctcagtg   3660
atccctcaag atccagtgct gctctcagga accatcagat tcaacctaga tccctttgac   3720
cgtcacactg accagcagat ctgggatgcc ttggagagga cattcctgac caaggccatc   3780
tcaaagttcc ccaaaaagct gcatacagat gtggtggaaa acggtggaaa cttctctgtg   3840
ggggagaggc agctgctctg cattgccagg ctgtgcttc gcaactccaa gatcatcctt   3900
atcgatgaag ccacagcctc cattgacatg gagacagaca ccctgatcca gcgcacaatc   3960
cgtgaagcct tccagggctg caccgtgctc gtcattgccc accgtgtcac cactgtgctg   4020
aactgtgacc acatcctggt tatgggcaat gggaaggtgg tagaatttga tcggccggag   4080
```

```
gtactgcgga agaagcctgg gtcattgttc gcagccctca tggccacagc cacttcttca    4140
ctgagataa                                                            4149
```

<210> SEQ ID NO 18
<211> LENGTH: 1379
<212> TYPE: PRT
<213> ORGANISM: homo sapiens

<400> SEQUENCE: 18

```
Met Thr Arg Lys Arg Thr Tyr Trp Val Pro Asn Ser Ser Gly Gly Leu
 1               5                  10                  15

Val Asn Arg Gly Ile Asp Ile Gly Asp Asp Met Val Ser Gly Leu Ile
            20                  25                  30

Tyr Lys Thr Tyr Thr Leu Gln Asp Gly Pro Trp Ser Gln Gln Glu Arg
        35                  40                  45

Asn Pro Glu Ala Pro Gly Arg Ala Ala Val Pro Pro Trp Gly Lys Tyr
    50                  55                  60

Asp Ala Ala Leu Arg Thr Met Ile Pro Phe Arg Pro Lys Pro Arg Phe
65                  70                  75                  80

Pro Ala Pro Gln Pro Leu Gly Leu Phe Ser Tyr Leu Thr Val Ser Trp
                85                  90                  95

Leu Thr Pro Leu Met Ile Gln Ser Leu Arg Ser Arg Leu Asp Glu Asn
            100                 105                 110

Thr Ile Pro Pro Leu Ser Val His Asp Ala Ser Asp Lys Asn Val Gln
        115                 120                 125

Arg Leu His Arg Leu Trp Glu Glu Val Ser Arg Gly Ile Glu
    130                 135                 140

Lys Ala Ser Val Leu Leu Val Met Leu Arg Phe Gln Arg Thr Arg Leu
145                 150                 155                 160

Ile Phe Asp Ala Leu Leu Gly Ile Cys Phe Cys Ile Ala Ser Val Leu
                165                 170                 175

Gly Pro Ile Leu Ile Ile Pro Lys Ile Leu Glu Tyr Ser Glu Glu Gln
            180                 185                 190

Leu Gly Asn Val Val His Gly Val Gly Leu Cys Phe Ala Leu Phe Leu
        195                 200                 205

Ser Glu Cys Val Lys Ser Leu Ser Phe Ser Ser Trp Ile Ile Asn
    210                 215                 220

Gln Arg Thr Ala Ile Arg Phe Gln Ala Ala Val Ser Ser Phe Ala Phe
225                 230                 235                 240

Glu Lys Leu Ile Gln Phe Lys Ser Val Ile His Ile Thr Ser Gly Glu
                245                 250                 255

Ala Ile Ser Phe Phe Thr Gly Asp Val Asn Tyr Leu Phe Glu Gly Val
            260                 265                 270

Cys Tyr Gly Pro Leu Val Leu Ile Thr Cys Ala Ser Leu Val Ile Cys
        275                 280                 285

Ser Ile Ser Ser Tyr Phe Ile Ile Gly Tyr Thr Ala Phe Ile Ala Ile
    290                 295                 300

Leu Cys Tyr Leu Leu Val Phe Pro Leu Glu Val Phe Met Thr Arg Met
305                 310                 315                 320

Ala Val Lys Ala Gln His His Thr Ser Glu Val Ser Asp Gln Arg Ile
                325                 330                 335

Arg Val Thr Ser Glu Val Leu Thr Cys Ile Lys Leu Ile Lys Met Tyr
            340                 345                 350
```

```
Thr Trp Glu Lys Pro Phe Ala Lys Ile Ile Glu Asp Leu Arg Arg Lys
        355                 360                 365

Glu Arg Lys Leu Leu Glu Lys Cys Gly Leu Val Gln Ser Leu Thr Ser
        370                 375                 380

Ile Thr Leu Phe Ile Ile Pro Thr Val Ala Thr Ala Val Trp Val Leu
385                 390                 395                 400

Ile His Thr Ser Leu Lys Leu Lys Leu Thr Ala Ser Met Ala Phe Ser
                    405                 410                 415

Met Leu Ala Ser Leu Asn Leu Leu Arg Leu Ser Val Phe Phe Val Pro
                420                 425                 430

Ile Ala Val Lys Gly Leu Thr Asn Ser Lys Ser Ala Val Met Arg Phe
            435                 440                 445

Lys Lys Phe Phe Leu Gln Glu Ser Pro Val Phe Tyr Val Gln Thr Leu
        450                 455                 460

Gln Asp Pro Ser Lys Ala Leu Val Phe Glu Glu Ala Thr Leu Ser Trp
465                 470                 475                 480

Gln Gln Thr Cys Pro Gly Ile Val Asn Gly Ala Leu Glu Leu Glu Arg
                    485                 490                 495

Asn Gly His Ala Ser Glu Gly Met Thr Arg Pro Arg Asp Ala Leu Gly
                500                 505                 510

Pro Glu Glu Glu Gly Asn Ser Leu Gly Pro Glu Leu His Lys Ile Asn
            515                 520                 525

Leu Val Val Ser Lys Gly Met Met Leu Gly Val Cys Gly Asn Thr Gly
        530                 535                 540

Ser Gly Lys Ser Ser Leu Leu Ser Ala Ile Leu Glu Glu Met His Leu
545                 550                 555                 560

Leu Glu Gly Ser Val Gly Val Gln Gly Ser Leu Ala Tyr Val Pro Gln
                    565                 570                 575

Gln Ala Trp Ile Val Ser Gly Asn Ile Arg Glu Asn Ile Leu Met Gly
                580                 585                 590

Gly Ala Tyr Asp Lys Ala Arg Tyr Leu Gln Val Leu His Cys Cys Ser
            595                 600                 605

Leu Asn Arg Asp Leu Glu Leu Leu Pro Phe Gly Asp Met Thr Glu Ile
        610                 615                 620

Gly Glu Arg Gly Leu Asn Leu Ser Gly Gly Gln Lys Gln Arg Ile Ser
625                 630                 635                 640

Leu Ala Arg Ala Val Tyr Ser Asp Arg Gln Ile Tyr Leu Leu Asp Asp
                    645                 650                 655

Pro Leu Ser Ala Val Asp Ala His Val Gly Lys His Ile Phe Glu Glu
                660                 665                 670

Cys Ile Lys Lys Thr Leu Arg Gly Lys Thr Val Leu Val Thr His
            675                 680                 685

Gln Leu Gln Tyr Leu Glu Phe Cys Gly Gln Ile Ile Leu Leu Glu Asn
        690                 695                 700

Gly Lys Ile Cys Glu Asn Gly Thr His Ser Glu Leu Met Gln Lys Lys
705                 710                 715                 720

Gly Lys Tyr Ala Gln Leu Ile Gln Lys Met His Lys Glu Ala Thr Ser
                    725                 730                 735

Asp Met Leu Gln Asp Thr Ala Lys Ile Ala Glu Lys Pro Lys Val Glu
                740                 745                 750

Ser Gln Ala Leu Ala Thr Ser Leu Glu Glu Ser Leu Asn Gly Asn Ala
            755                 760                 765

Val Pro Glu His Gln Leu Thr Gln Glu Glu Glu Met Glu Glu Gly Ser
```

```
         770                 775                 780
Leu Ser Trp Arg Val Tyr His His Tyr Ile Gln Ala Gly Gly Tyr
785                 790                 795                 800

Met Val Ser Cys Ile Ile Phe Phe Val Leu Ile Val Phe Leu
                    805                 810                 815

Thr Ile Phe Ser Phe Trp Trp Leu Ser Tyr Trp Leu Glu Gln Gly Ser
                    820                 825                 830

Gly Thr Asn Ser Ser Arg Glu Ser Asn Gly Thr Met Ala Asp Leu Gly
                    835                 840                 845

Asn Ile Ala Asp Asn Pro Gln Leu Ser Phe Tyr Gln Leu Val Tyr Gly
850                 855                 860

Leu Asn Ala Leu Leu Leu Ile Cys Val Gly Val Cys Ser Ser Gly Ile
865                 870                 875                 880

Phe Thr Lys Val Thr Arg Lys Ala Ser Thr Ala Leu His Asn Lys Leu
                    885                 890                 895

Phe Asn Lys Val Phe Arg Cys Pro Met Ser Phe Asp Thr Ile Pro
                900                 905                 910

Ile Gly Arg Leu Leu Asn Cys Phe Ala Gly Asp Leu Glu Gln Leu Asp
                915                 920                 925

Gln Leu Leu Pro Ile Phe Ser Glu Gln Phe Leu Val Leu Ser Leu Met
            930                 935                 940

Val Ile Ala Val Leu Leu Ile Val Ser Val Leu Ser Pro Tyr Ile Leu
945                 950                 955                 960

Leu Met Gly Ala Ile Ile Met Val Ile Cys Phe Ile Tyr Tyr Met Met
                965                 970                 975

Phe Lys Lys Ala Ile Gly Val Phe Lys Arg Leu Glu Asn Tyr Ser Arg
                980                 985                 990

Ser Pro Leu Phe Ser His Ile Leu Asn Ser Leu Gln Gly Leu Ser Ser
                995                 1000                1005

Ile His Val Tyr Gly Lys Thr Glu Asp Phe Ile Ser Gln Phe Lys Arg
            1010                1015                1020

Leu Thr Asp Ala Gln Asn Asn Tyr Leu Leu Leu Phe Leu Ser Ser Thr
1025                1030                1035                1040

Arg Trp Met Ala Leu Arg Leu Glu Ile Met Thr Asn Leu Val Thr Leu
                1045                1050                1055

Ala Val Ala Leu Phe Val Ala Phe Gly Ile Ser Ser Thr Pro Tyr Ser
                1060                1065                1070

Phe Lys Val Met Ala Val Asn Ile Val Leu Gln Leu Ala Ser Ser Phe
            1075                1080                1085

Gln Ala Thr Ala Arg Ile Gly Leu Glu Thr Glu Ala Gln Phe Thr Ala
            1090                1095                1100

Val Glu Arg Ile Leu Gln Tyr Met Lys Met Cys Val Ser Glu Ala Pro
1105                1110                1115                1120

Leu His Met Glu Gly Thr Ser Cys Pro Gln Gly Trp Pro Gln His Gly
                    1125                1130                1135

Glu Ile Ile Phe Gln Asp Tyr His Met Lys Tyr Arg Asp Asn Thr Pro
                    1140                1145                1150

Thr Val Leu His Gly Ile Asn Leu Thr Ile Arg Gly His Glu Val Val
            1155                1160                1165

Gly Ile Val Gly Arg Thr Gly Ser Gly Lys Ser Ser Leu Gly Met Ala
        1170                1175                1180

Leu Phe Arg Leu Val Glu Pro Met Ala Gly Arg Ile Leu Ile Asp Gly
1185                1190                1195                1200
```

-continued

Val Asp Ile Cys Ser Ile Gly Leu Glu Asp Leu Arg Ser Lys Leu Ser
               1205                1210                1215

Val Ile Pro Gln Asp Pro Val Leu Leu Ser Gly Thr Ile Arg Phe Asn
            1220                1225                1230

Leu Asp Pro Phe Asp Arg His Thr Asp Gln Gln Ile Trp Asp Ala Leu
        1235                1240                1245

Glu Arg Thr Phe Leu Thr Lys Ala Ile Ser Lys Phe Pro Lys Lys Leu
    1250                1255                1260

His Thr Asp Val Val Glu Asn Gly Gly Asn Phe Ser Val Gly Glu Arg
1265                1270                1275                1280

Gln Leu Leu Cys Ile Ala Arg Ala Val Leu Arg Asn Ser Lys Ile Ile
                1285                1290                1295

Leu Ile Asp Glu Ala Thr Ala Ser Ile Asp Met Glu Thr Asp Thr Leu
            1300                1305                1310

Ile Gln Arg Thr Ile Arg Glu Ala Phe Gln Gly Cys Thr Val Leu Val
        1315                1320                1325

Ile Ala His Arg Val Thr Thr Val Leu Asn Cys Asp His Ile Leu Val
    1330                1335                1340

Met Gly Asn Gly Lys Val Val Glu Phe Asp Arg Pro Glu Val Leu Arg
1345                1350                1355                1360

Lys Lys Pro Gly Ser Leu Phe Ala Ala Leu Met Ala Thr Ala Thr Ser
                1365                1370                1375

Ser Leu Arg

<210> SEQ ID NO 19
<211> LENGTH: 2448
<212> TYPE: DNA
<213> ORGANISM: homo sapiens

<400> SEQUENCE: 19
atgactagga agaggacata ctgggtgccc aactcttctg gtggcctcgt gaatcgtggc      60
atcgacatag gcgatgacat ggtttcagga cttatttata aaacctatac tctccaagat    120
ggcccctgga gtcagcaaga gagaaatcct gaggctccag ggagggcagc tgtcccaccg    180
tgggggaagt atgatgctgc cttgagaacc atgattccct tccgtcccaa gccgaggttt    240
cctgcccccc agcccctgga caatgctggc ctgttctcct acctcaccgt gtcatggctc    300
accccgctca tgatccaaag cttacggagt cgcttagatg agaacaccat ccctccactg    360
tcagtccatg atgcctcaga caaaaatgtc caaaggcttc accgcctttg ggaagaagaa    420
gtctcaaggc gagggattga aaaagcttca gtgcttctgg tgatgctgag gttccagaga    480
acaaggttga ttttcgatgc acttctgggc atctgcttct gcattgccag tgtactcggg    540
ccaatattga ttataccaaa gatcctggaa tattcagaag agcagttggg gaatgttgtc    600
catggagtgg gactctgctt tgccttttt ctctccgaat gtgtgaagtc tctgagtttc    660
tcctccagtt ggatcatcaa ccaacgcaca gccatcaggt tccaagcagc tgtttcctcc    720
tttgcctttg agaagctcat ccaatttaag tctgtaatac acatcacctc aggagaggcc    780
atcagcttct tcaccggtga tgtaaactac ctgtttgaag gggtgtgcta tggacccta    840 gtactgatca cctgcgcatc gctggtcatc tgcagcattt cttcctactt cattattgga    900
tacactgcat ttattgccat cttatgctat ctcctggttt tcccactgga ggtattcatg    960
acaagaatgg ctgtgaaggc tcagcatcac acatctgagg tcagcgacca gcgcatccgt   1020
gtgaccagtg aagttctcac ttgcattaag ctgattaaaa tgtacacatg ggagaaacca   1080

-continued

```
tttgcaaaaa tcattgaaga cctaagaagg aaggaaagga agctattgga gaagtgcggg    1140
cttgtccaga gcctgacaag tataaccttg ttcatcatcc ccacagtggc cacagcggtc    1200
tgggttctca tccacacatc cttaaagctg aaactcacag cgtcaatggc cttcagcatg    1260
ctggcctcct tgaatctcct tcggctgtca gtgttctttg tgcctattgc agtcaaaggt    1320
ctcacgaatt ccaagtctgc agtgatgagg ttcaagaagt ttttcctcca ggagagccct    1380
gttttctatg tccagacatt acaagacccc agcaaagctc tggtctttga ggaggccacc    1440
ttgtcatggc aacagacctg tcccgggatc gtcaatgggg cactggagct ggagaggaac    1500
gggcatgctt ctgaggggat gaccaggcct agagatgccc tcgggccaga ggaagaaggg    1560
aacagcctgg gcccagagtt gcacaagatc aacctggtgg tgtccaaggg gatgatgtta    1620
ggggtctgcg gcaacacggg gagtggtaag agcagcctgt tgtcagccat cctggaggag    1680
atgcacttgc tcgagggctc ggtgggggtg cagggaagcc tggcctatgt cccccagcag    1740
gcctggatcg tcagcgggaa catcagggag aacatcctca tgggaggcgc atatgacaag    1800
gcccgatacc tccaggtgct ccactgctgc tccctgaatc gggacctgga acttctgccc    1860
tttggagaca tgacagagat tggagagcgg ggcctcaacc tctctggggg gcagaaacag    1920
aggatcagcc tggcccgcgc cgtctattcc gaccgtcaga tctacctgct ggacgacccc    1980
ctgtctgctg tggacgccca cgtggggaag cacattttg aggagtgcat taagaagaca    2040
ctcaggggga agacggtcgt cctggtgacc caccagctgc agtacttaga attttgtggc    2100
cagatcattt tgttggaaaa tgggaaaatc tgtgaaaatg gaactcacag tgagttaatg    2160
cagaaaaagg ggaaatatgc ccaacttatc cagaagatgc acaaggaagc cacttcggtt    2220
ttccgctgcc ccatgagttt ctttgacacc atcccaatag gccggctttt gaactgcttc    2280 gcagggact tggaacagct ggaccagctc ttgcccatct tttcagagca gttcctggtc    2340
ctgtccttaa tggtgatcgc cgtcctgttg attgtcagtg tgctgtctcc atatatcctg    2400
ttaatgggag ccataatcat ggttatttgc ttcatttatt atatgtga              2448
```

<210> SEQ ID NO 20
<211> LENGTH: 812
<212> TYPE: PRT
<213> ORGANISM: homo sapiens

<400> SEQUENCE: 20

```
Met Thr Arg Lys Arg Thr Tyr Trp Val Pro Asn Ser Ser Gly Gly Leu
  1               5                  10                  15

Val Asn Arg Gly Ile Asp Ile Gly Asp Asp Met Val Ser Gly Leu Ile
             20                  25                  30

Tyr Lys Thr Tyr Thr Leu Gln Asp Gly Pro Trp Ser Gln Gln Glu Arg
         35                  40                  45

Asn Pro Glu Ala Pro Gly Arg Ala Ala Val Pro Trp Gly Lys Tyr
     50                  55                  60

Asp Ala Ala Leu Arg Thr Met Ile Pro Phe Arg Pro Lys Pro Arg Phe
 65                  70                  75                  80

Pro Ala Pro Gln Pro Leu Gly Leu Phe Ser Tyr Leu Thr Val Ser Trp
                 85                  90                  95

Leu Thr Pro Leu Met Ile Gln Ser Leu Arg Ser Arg Leu Asp Glu Asn
                100                 105                 110

Thr Ile Pro Pro Leu Ser Val His Asp Ala Ser Asp Lys Asn Val Gln
            115                 120                 125
```

```
Arg Leu His Arg Leu Trp Glu Glu Val Ser Arg Arg Gly Ile Glu
    130                 135                 140

Lys Ala Ser Val Leu Leu Val Met Leu Arg Phe Gln Arg Thr Arg Leu
145                 150                 155                 160

Ile Phe Asp Ala Leu Leu Gly Ile Cys Phe Cys Ile Ala Ser Val Leu
                165                 170                 175

Gly Pro Ile Leu Ile Ile Pro Lys Ile Leu Glu Tyr Ser Glu Glu Gln
                180                 185                 190

Leu Gly Asn Val Val His Gly Val Gly Leu Cys Phe Ala Leu Phe Leu
            195                 200                 205

Ser Glu Cys Val Lys Ser Leu Ser Phe Ser Ser Trp Ile Ile Asn
    210                 215                 220

Gln Arg Thr Ala Ile Arg Phe Gln Ala Ala Val Ser Ser Phe Ala Phe
225                 230                 235                 240

Glu Lys Leu Ile Gln Phe Lys Ser Val Ile His Ile Thr Ser Gly Glu
                245                 250                 255

Ala Ile Ser Phe Phe Thr Gly Asp Val Asn Tyr Leu Phe Glu Gly Val
                260                 265                 270

Cys Tyr Gly Pro Leu Val Leu Ile Thr Cys Ala Ser Leu Val Ile Cys
        275                 280                 285

Ser Ile Ser Ser Tyr Phe Ile Ile Gly Tyr Thr Ala Phe Ile Ala Ile
    290                 295                 300

Leu Cys Tyr Leu Leu Val Phe Pro Leu Glu Val Phe Met Thr Arg Met
305                 310                 315                 320

Ala Val Lys Ala Gln His His Thr Ser Glu Val Ser Asp Gln Arg Ile
                325                 330                 335

Arg Val Thr Ser Glu Val Leu Thr Cys Ile Lys Leu Ile Lys Met Tyr
            340                 345                 350

Thr Trp Glu Lys Pro Phe Ala Lys Ile Ile Glu Asp Leu Arg Arg Lys
        355                 360                 365

Glu Arg Lys Leu Leu Glu Lys Cys Gly Leu Val Gln Ser Leu Thr Ser
    370                 375                 380

Ile Thr Leu Phe Ile Ile Pro Thr Val Ala Thr Ala Val Trp Val Leu
385                 390                 395                 400

Ile His Thr Ser Leu Lys Leu Lys Leu Thr Ala Ser Met Ala Phe Ser
                405                 410                 415

Met Leu Ala Ser Leu Asn Leu Leu Arg Leu Ser Val Phe Phe Val Pro
                420                 425                 430

Ile Ala Val Lys Gly Leu Thr Asn Ser Lys Ser Ala Val Met Arg Phe
            435                 440                 445

Lys Lys Phe Phe Leu Gln Glu Ser Pro Val Phe Tyr Val Gln Thr Leu
    450                 455                 460

Gln Asp Pro Ser Lys Ala Leu Val Phe Glu Glu Ala Thr Leu Ser Trp
465                 470                 475                 480

Gln Gln Thr Cys Pro Gly Ile Val Asn Gly Ala Leu Glu Leu Glu Arg
                485                 490                 495

Asn Gly His Ala Ser Glu Gly Met Thr Arg Pro Arg Asp Ala Leu Gly
            500                 505                 510

Pro Glu Glu Glu Gly Asn Ser Leu Gly Pro Glu Leu His Lys Ile Asn
    515                 520                 525

Leu Val Val Ser Lys Gly Met Met Leu Gly Val Cys Gly Asn Thr Gly
    530                 535                 540

Ser Gly Lys Ser Ser Leu Leu Ser Ala Ile Leu Glu Glu Met His Leu
```

```
                545                 550                 555                 560
Leu Glu Gly Ser Val Gly Val Gln Gly Ser Leu Ala Tyr Val Pro Gln
                    565                 570                 575
Gln Ala Trp Ile Val Ser Gly Asn Ile Arg Glu Asn Ile Leu Met Gly
                580                 585                 590
Gly Ala Tyr Asp Lys Ala Arg Tyr Leu Gln Val Leu His Cys Cys Ser
            595                 600                 605
Leu Asn Arg Asp Leu Glu Leu Leu Pro Phe Gly Asp Met Thr Glu Ile
        610                 615                 620
Gly Glu Arg Gly Leu Asn Leu Ser Gly Gly Gln Lys Gln Arg Ile Ser
625                 630                 635                 640
Leu Ala Arg Ala Val Tyr Ser Asp Arg Gln Ile Tyr Leu Leu Asp Asp
                645                 650                 655
Pro Leu Ser Ala Val Asp Ala His Val Gly Lys His Ile Phe Glu Glu
            660                 665                 670
Cys Ile Lys Lys Thr Leu Arg Gly Lys Thr Val Leu Val Thr His
        675                 680                 685
Gln Leu Gln Tyr Leu Glu Phe Cys Gly Gln Ile Ile Leu Leu Glu Asn
    690                 695                 700
Gly Lys Ile Cys Glu Asn Gly Thr His Ser Glu Leu Met Gln Lys Lys
705                 710                 715                 720
Gly Lys Tyr Ala Gln Leu Ile Gln Lys Met His Lys Glu Ala Thr Ser
                725                 730                 735
Val Phe Arg Cys Pro Met Ser Phe Phe Asp Thr Ile Pro Ile Gly Arg
            740                 745                 750
Leu Leu Asn Cys Phe Ala Gly Asp Leu Glu Gln Leu Asp Gln Leu Leu
        755                 760                 765
Pro Ile Phe Ser Glu Gln Phe Leu Val Leu Ser Leu Met Val Ile Ala
    770                 775                 780
Val Leu Leu Ile Val Ser Val Leu Ser Pro Tyr Ile Leu Leu Met Gly
785                 790                 795                 800
Ala Ile Ile Met Val Ile Cys Phe Ile Tyr Tyr Met
                805                 810

<210> SEQ ID NO 21
<211> LENGTH: 2586
<212> TYPE: DNA
<213> ORGANISM: homo sapiens

<400> SEQUENCE: 21
atgactagga agaggacata ctgggtgccc aactcttctg gtggcctcgt gaatcgtggc    60
atcgacatag gcgatgacat ggtttcagga cttatttata aaacctatac tctccaagat   120
ggcccctgga gtcagcaaga gagaaatcct gaggctccag ggagggcagc tgtcccaccg   180
tgggggaagt atgatgctgc cttgagaacc atgattccct ccgtcccaa gccgaggttt    240
cctgccccc agcccctgga caatgctggc ctgttctcct acctcaccgt gtcatggctc   300
accccgctca tgatccaaag cttacggagt cgcttagatg agaacaccat ccctccactg   360
tcagtccatg atgcctcaga caaaaatgtc caaaggcttc accgcctttg ggaagaagaa   420
gtctcaaggc gagggattga aaaagcttca gtgcttctgg tgatgctgag gttccagaga   480
acaaggttga ttttcgatgc acttctgggc atctgcttct gcattgccag tgtactcggg   540
ccaatattga ttataccaaa gatcctggaa tattcagaag agcagttggg gaatgttgtc   600
catggagtgg gactctgctt tgcccttttt ctctccgaat gtgtgaagtc tctgagtttc   660
```

-continued

```
tcctccagtt ggatcatcaa ccaacgcaca gccatcaggt tccaagcagc tgtttcctcc      720
tttgcctttg agaagctcat ccaatttaag tctgtaatac acatcacctc aggagaggcc      780
atcagcttct tcaccggtga tgtaaactac ctgtttgaag gggtgtgcta tggaccccta      840
gtactgatca cctgcgcatc gctggtcatc tgcagcattt cttcctactt cattattgga      900
tacactgcat ttattgccat cttatgctat ctcctggttt tcccactgga ggtattcatg      960
acaagaatgg ctgtgaaggc tcagcatcac acatctgagg tcagcgacca gcgcatccgt     1020
gtgaccagtg aagttctcac ttgcattaag ctgattaaaa tgtacacatg ggagaaacca     1080
tttgcaaaaa tcattgaaga cctaagaagg aaggaaagga agctattgga gaagtgcggg     1140
cttgtccaga gcctgacaag tataaccttg ttcatcatcc cacagtggc cacagcggtc      1200
tgggttctca tccacacatc cttaaagctg aaactcacag cgtcaatggc cttcagcatg     1260
ctggcctcct tgaatctcct tcggctgtca gtgttctttg tgcctattgc agtcaaaggt     1320
ctcacgaatt ccaagtctgc agtgatgagg ttcaagaagt ttttcctcca ggagagccct     1380
gttttctatg tccagacatt acaagacccc agcaaagctc tggtctttga ggaggccacc     1440
ttgtcatggc aacagacctg tcccgggatc gtcaatgggg cactggagct ggagaggaac     1500
gggcatgctt ctgaggggat gaccaggcct agagatgccc tcgggccaga ggaagaaggg     1560
aacagcctgg gcccagagtt gcacaagatc aacctggtgg tgtccaaggg gatgatgtta     1620
ggggtctgcg gcaacacggg gagtggtaag agcagcctgt tgtcagccat cctggaggag     1680
atgcacttgc tcgagggctc ggtggggtgt cagggaagcc tggcctatgt cccccagcag     1740
gcctggatcg tcagcgggaa catcaggag aacatcctca tgggaggcgc atatgacaag     1800
gcccgatacc tccaggtgct ccactgctgc tccctgaatc gggacctgga acttctgccc     1860
tttggagaca tgacagagat tggagagcgg ggcctcaacc tctctggggg gcagaaacag     1920
aggatcagcc tggcccgcgc cgtctattcc gaccgtcaga tctacctgct ggacgacccc     1980
ctgtctgctg tggacgccca cgtggggaag cacattttg aggagtgcat taagaagaca     2040
ctcaggggga gacggtcgt cctggtgacc accagctgc agtacttaga atttttgtggc     2100
cagatcattt tgttggaaaa tgggaaaatc tgtgaaaatg gaactcacag tgagttaatg     2160
cagaaaaagg ggaaatatgc ccaacttatc cagaagatgc acaaggaagc cacttcggtt     2220
ttccgctgcc ccatgagttt ctttgacacc atcccaatag gccggctttt gaactgcttc     2280
gcagggact tggaacagct ggaccagctc ttgcccatct tttcagagca gttcctggtc     2340
ctgtccttaa tggtgatcgc cgtcctgttg attgtcagtg tgctgtctcc atatatcctg     2400
ttaatgggag ccataatcat ggttatttgc ttcatttatt atatgatgtt caagaaggcc     2460
atcggtgtgt tcaagagact ggagaactat agccggtctc ctttattctc ccacatcctc     2520
aattctctgc aaggcctgag ctccatccat gtctatggaa aaactgaaga cttcatcagc     2580
cagtga                                                                2586
```

<210> SEQ ID NO 22
<211> LENGTH: 858
<212> TYPE: PRT
<213> ORGANISM: homo sapiens

<400> SEQUENCE: 22

```
Met Thr Arg Lys Arg Thr Tyr Trp Val Pro Asn Ser Ser Gly Gly Leu
 1               5                  10                  15

Val Asn Arg Gly Ile Asp Ile Gly Asp Asp Met Val Ser Gly Leu Ile
```

-continued

```
                20                  25                  30
Tyr Lys Thr Tyr Thr Leu Gln Asp Gly Pro Trp Ser Gln Gln Glu Arg
        35                  40                  45

Asn Pro Glu Ala Pro Gly Arg Ala Ala Val Pro Pro Trp Gly Lys Tyr
 50                  55                  60

Asp Ala Ala Leu Arg Thr Met Ile Pro Phe Arg Pro Lys Pro Arg Phe
 65                  70                  75                  80

Pro Ala Pro Gln Pro Leu Gly Leu Phe Ser Tyr Leu Thr Val Ser Trp
                 85                  90                  95

Leu Thr Pro Leu Met Ile Gln Ser Leu Arg Ser Arg Leu Asp Glu Asn
                100                 105                 110

Thr Ile Pro Pro Leu Ser Val His Asp Ala Ser Asp Lys Asn Val Gln
                115                 120                 125

Arg Leu His Arg Leu Trp Glu Glu Val Ser Arg Gly Ile Glu
                130                 135                 140

Lys Ala Ser Val Leu Val Met Leu Arg Phe Gln Arg Thr Arg Leu
145                 150                 155                 160

Ile Phe Asp Ala Leu Leu Gly Ile Cys Phe Cys Ile Ala Ser Val Leu
                165                 170                 175

Gly Pro Ile Leu Ile Pro Lys Ile Leu Glu Tyr Ser Glu Glu Gln
                180                 185                 190

Leu Gly Asn Val Val His Gly Val Gly Leu Cys Phe Ala Leu Phe Leu
                195                 200                 205

Ser Glu Cys Val Lys Ser Leu Ser Phe Ser Ser Trp Ile Ile Asn
                210                 215                 220

Gln Arg Thr Ala Ile Arg Phe Gln Ala Ala Val Ser Ser Phe Ala Phe
225                 230                 235                 240

Glu Lys Leu Ile Gln Phe Lys Ser Val Ile His Ile Thr Ser Gly Glu
                245                 250                 255

Ala Ile Ser Phe Phe Thr Gly Asp Val Asn Tyr Leu Phe Glu Gly Val
                260                 265                 270

Cys Tyr Gly Pro Leu Val Leu Ile Thr Cys Ala Ser Leu Val Ile Cys
                275                 280                 285

Ser Ile Ser Ser Tyr Phe Ile Ile Gly Tyr Thr Ala Phe Ile Ala Ile
                290                 295                 300

Leu Cys Tyr Leu Leu Val Phe Pro Leu Glu Val Phe Met Thr Arg Met
305                 310                 315                 320

Ala Val Lys Ala Gln His His Thr Ser Glu Val Ser Asp Gln Arg Ile
                325                 330                 335

Arg Val Thr Ser Glu Val Leu Thr Cys Ile Lys Leu Ile Lys Met Tyr
                340                 345                 350

Thr Trp Glu Lys Pro Phe Ala Lys Ile Ile Glu Asp Leu Arg Arg Lys
                355                 360                 365

Glu Arg Lys Leu Leu Glu Lys Cys Gly Leu Val Gln Ser Leu Thr Ser
        370                 375                 380

Ile Thr Leu Phe Ile Ile Pro Thr Val Ala Thr Ala Val Trp Val Leu
385                 390                 395                 400

Ile His Thr Ser Leu Lys Leu Lys Leu Thr Ala Ser Met Ala Phe Ser
                405                 410                 415

Met Leu Ala Ser Leu Asn Leu Leu Arg Leu Ser Val Phe Phe Val Pro
                420                 425                 430

Ile Ala Val Lys Gly Leu Thr Asn Ser Lys Ser Ala Val Met Arg Phe
                435                 440                 445
```

```
Lys Lys Phe Phe Leu Gln Glu Ser Pro Val Phe Tyr Val Gln Thr Leu
    450                 455                 460

Gln Asp Pro Ser Lys Ala Leu Val Phe Glu Glu Ala Thr Leu Ser Trp
465                 470                 475                 480

Gln Gln Thr Cys Pro Gly Ile Val Asn Gly Ala Leu Glu Leu Glu Arg
                485                 490                 495

Asn Gly His Ala Ser Glu Gly Met Thr Arg Pro Arg Asp Ala Leu Gly
            500                 505                 510

Pro Glu Glu Gly Asn Ser Leu Gly Pro Glu Leu His Lys Ile Asn
        515                 520                 525

Leu Val Val Ser Lys Gly Met Met Leu Gly Val Cys Gly Asn Thr Gly
    530                 535                 540

Ser Gly Lys Ser Ser Leu Leu Ser Ala Ile Leu Glu Glu Met His Leu
545                 550                 555                 560

Leu Glu Gly Ser Val Gly Val Gln Gly Ser Leu Ala Tyr Val Pro Gln
                565                 570                 575

Gln Ala Trp Ile Val Ser Gly Asn Ile Arg Glu Asn Ile Leu Met Gly
            580                 585                 590

Gly Ala Tyr Asp Lys Ala Arg Tyr Leu Gln Val Leu His Cys Cys Ser
        595                 600                 605

Leu Asn Arg Asp Leu Glu Leu Leu Pro Phe Gly Asp Met Thr Glu Ile
    610                 615                 620

Gly Glu Arg Gly Leu Asn Leu Ser Gly Gly Gln Lys Gln Arg Ile Ser
625                 630                 635                 640

Leu Ala Arg Ala Val Tyr Ser Asp Arg Gln Ile Tyr Leu Leu Asp Asp
                645                 650                 655

Pro Leu Ser Ala Val Asp Ala His Val Gly Lys His Ile Phe Glu Glu
            660                 665                 670

Cys Ile Lys Lys Thr Leu Arg Gly Lys Thr Val Val Leu Val Thr His
        675                 680                 685

Gln Leu Gln Tyr Leu Glu Phe Cys Gly Gln Ile Ile Leu Leu Glu Asn
    690                 695                 700

Gly Lys Ile Cys Glu Asn Gly Thr His Ser Glu Leu Met Gln Lys Lys
705                 710                 715                 720

Gly Lys Tyr Ala Gln Leu Ile Gln Lys Met His Lys Glu Ala Thr Ser
                725                 730                 735

Val Phe Arg Cys Pro Met Ser Phe Phe Asp Thr Ile Pro Ile Gly Arg
            740                 745                 750

Leu Leu Asn Cys Phe Ala Gly Asp Leu Glu Gln Leu Asp Gln Leu Leu
        755                 760                 765

Pro Ile Phe Ser Glu Gln Phe Leu Val Leu Ser Leu Met Val Ile Ala
    770                 775                 780

Val Leu Leu Ile Val Ser Val Leu Ser Pro Tyr Ile Leu Leu Met Gly
785                 790                 795                 800

Ala Ile Ile Met Val Ile Cys Phe Ile Tyr Tyr Met Met Phe Lys Lys
                805                 810                 815

Ala Ile Gly Val Phe Lys Arg Leu Glu Asn Tyr Ser Arg Ser Pro Leu
            820                 825                 830

Phe Ser His Ile Leu Asn Ser Leu Gln Gly Leu Ser Ser Ile His Val
        835                 840                 845

Tyr Gly Lys Thr Glu Asp Phe Ile Ser Gln
    850                 855
```

<210> SEQ ID NO 23
<211> LENGTH: 3660
<212> TYPE: DNA
<213> ORGANISM: homo sapiens

<400> SEQUENCE: 23

| | | | | | |
|---|---|---|---|---|---|
| atgactagga | agaggacata | ctgggtgccc | aactcttctg | gtggcctcgt | gaatcgtggc | 60 |
| atcgacatag | gcgatgacat | ggtttcagga | cttatttata | aaacctatac | tctccaagat | 120 |
| ggccccctgga | gtcagcaaga | gagaaatcct | gaggctccag | ggagggcagc | tgtcccaccg | 180 |
| tgggggaagt | atgatgctgc | cttgagaacc | atgattccct | tccgtcccaa | gccgaggttt | 240 |
| cctgccccc | agcccctgga | caatgctggc | ctgttctcct | acctcaccgt | gtcatggctc | 300 |
| accccgctca | tgatccaaag | cttacggagt | cgcttagatg | agaacaccat | ccctccactg | 360 |
| tcagtccatg | atgcctcaga | caaaaatgtc | caaaggcttc | accgcctttg | ggaagaagaa | 420 |
| gtctcaaggc | gagggattga | aaaagcttca | gtgcttctgg | tgatgctgag | gttccagaga | 480 |
| acaaggttga | ttttcgatgc | acttctgggc | atctgcttct | gcattgccag | tgtactcggg | 540 |
| ccaatattga | ttataccaaa | gatcctggaa | tattcagaag | agcagttggg | gaatgttgtc | 600 |
| catggagtgg | gactctgctt | tgccctttt | ctctccgaat | gtgtgaagtc | tctgagtttc | 660 |
| tcctccagtt | ggatcatcaa | ccaacgcaca | gccatcaggt | tccaagcagc | tgtttcctcc | 720 |
| tttgcctttg | agaagctcat | ccaatttaag | tctgtaatac | acatcacctc | aggagaggcc | 780 |
| atcagcttct | tcaccggtga | tgtaaactac | ctgtttgaag | gggtgtgcta | tgacccccta | 840 |
| gtactgatca | cctgcgcatc | gctggtcatc | tgcagcattt | cttcctactt | cattattgga | 900 |
| tacactgcat | ttattgccat | cttatgctat | ctcctggttt | tcccactgga | ggtattcatg | 960 |
| acaagaatgg | ctgtgaaggc | tcagcatcac | acatctgagg | tcagcgacca | gcgcatccgt | 1020 |
| gtgaccagtg | aagttctcac | ttgcattaag | ctgattaaaa | tgtacacatg | ggagaaacca | 1080 |
| tttgcaaaaa | tcattgaaga | cctaagaagg | aaggaaagga | agctattgga | gaagtgcggg | 1140 |
| cttgtccaga | gcctgacaag | tataaccttg | ttcatcatcc | ccacagtggc | cacagcggtc | 1200 |
| tgggttctca | tccacacatc | cttaaagctg | aaactcacag | cgtcaatggc | cttcagcatg | 1260 |
| ctggcctcct | tgaatctcct | tcggctgtca | gtgttctttg | tgcctattgc | agtcaaaggt | 1320 |
| ctcacgaatt | ccaagtctgc | agtgatgagg | ttcaagaagt | ttttcctcca | ggagagccct | 1380 |
| gttttctatg | tccagacatt | acaagacccc | agcaaagctc | tggtctttga | ggaggccacc | 1440 |
| ttgtcatggc | aacagacctg | tcccgggatc | gtcaatgggg | cactggagct | ggagaggaac | 1500 |
| gggcatgctt | ctgagggat | gaccaggcct | agagatgccc | tcgggccaga | ggaagaaggg | 1560 |
| aacagcctgg | gccagagtt | gcacaagatc | aacctggtgg | tgtccaaggg | gatgatgtta | 1620 |
| ggggtctgcg | gcaacacggg | gagtggtaag | agcagcctgt | tgtcagccat | cctggaggag | 1680 |
| atgcacttgc | tcgagggctc | ggtggggtg | cagggaagcc | tggcctatgt | cccccagcag | 1740 |
| gcctggatcg | tcagcgggaa | catcagggag | aacatcctca | tgggaggcgc | atatgacaag | 1800 |
| gcccgatacc | tccaggtgct | ccactgctgc | tccctgaatc | gggacctgga | acttctgccc | 1860 |
| tttggagaca | tgacagagat | tggagagcgg | ggcctcaacc | tctctggggg | gcagaaacag | 1920 |
| aggatcagcc | tggcccgcgc | cgtctattcc | gaccgtcaga | tctacctgct | ggacgacccc | 1980 |
| ctgtctgctg | tggacgccca | cgtggggaag | cacattttg | aggagtgcat | taagaagaca | 2040 |
| ctcagggggga | agacggtcgt | cctggtgacc | caccagctgc | agtacttaga | attttgtggc | 2100 |
| cagatcattt | tgttggaaaa | tgggaaaatc | tgtgaaaatg | gaactcacag | tgagttaatg | 2160 |

-continued

```
cagaaaaagg ggaaatatgc ccaacttatc cagaagatgc acaaggaagc cacttcggtt    2220
ttccgctgcc ccatgagttt ctttgacacc atcccaatag gccggctttt gaactgcttc    2280 gcagggact tggaacagct ggaccagctc ttgcccatct tttcagagca gttcctggtc     2340
ctgtccttaa tggtgatcgc cgtcctgttg attgtcagtg tgctgtctcc atatatcctg   2400
ttaatgggag ccataatcat ggttatttgc ttcatttatt atatgatgtt caagaaggcc    2460
atcggtgtgt tcaagagact ggagaactat agccggtctc ctttattctc ccacatcctc   2520
aattctctgc aaggcctgag ctccatccat gtctatggaa aaactgaaga cttcatcagc   2580
cagtttaaga ggctgactga tgcgcagaat aactacctgc tgttgtttct atcttccaca   2640
cgatggatgg cattgaggct ggagatcatg accaaccttg tgccttggc tgttgccctg    2700 ttcgtggctt ttggcatttc ctccaccccc tactccttta agtcatggc tgtcaacatc    2760 gtgctgcagc tggcgtccag cttccaggcc actgcccgga ttggcttgga cagagaggca   2820
cagttcacgg ctgtagagag gatactgcag tacatgaaga tgtgtgtctc ggaagctcct   2880
ttacacatgg aaggcacaag ttgtccccag gggtggccac agcatgggga aatcatattt   2940
caggattatc acatgaaata cagagacaac acacccaccg tgcttcacgg catcaacctg   3000
accatccgcg ccacgaagt ggtgggcatc gtgggaagga cgggctctgg gaagtcctcc    3060
ttgggcatgg ctctcttccg cctggtggag cccatggcag gccggattct cattgacggc   3120
gtggacattt gcagcatcgg cctggaggac ttgcggtcca agctctcagt gatccctcaa   3180
gatccagtgc tgctctcagg aaccatcaga ttcaacctag atcccttga ccgtcacact    3240 gaccagcaga tctgggatgc cttggagagg acattcctga ccaaggccat ctcaaagttc   3300
cccaaaaagc tgcatacaga tgtggtgaa acggtggaa acttctctgt gggggagagg     3360
cagctgctct gcattgccag ggctgtgctt cgcaactcca agatcatcct tatcgatgaa   3420
gccacagcct ccattgacat ggagacagac accctgatcc agcgcacaat ccgtgaagcc   3480
ttccagggct gcaccgtgct cgtcattgcc caccgtgtca ccactgtgct gaactgtgac   3540
cacatcctgg ttatgggcaa tgggaaggtg gtagaatttg atcggccgga ggtactgcgg   3600
aagaagcctg ggtcattgtt cgcagccctc atggccacag ccacttcttc actgagataa   3660
```

<210> SEQ ID NO 24
<211> LENGTH: 1216
<212> TYPE: PRT
<213> ORGANISM: homo sapiens

<400> SEQUENCE: 24

```
Met Thr Arg Lys Arg Thr Tyr Trp Val Pro Asn Ser Ser Gly Gly Leu
  1               5                  10                  15

Val Asn Arg Gly Ile Asp Ile Gly Asp Asp Met Val Ser Gly Leu Ile
             20                  25                  30

Tyr Lys Thr Tyr Thr Leu Gln Asp Gly Pro Trp Ser Gln Gln Glu Arg
         35                  40                  45

Asn Pro Glu Ala Pro Gly Arg Ala Ala Val Pro Trp Gly Lys Tyr
 50                  55                  60

Asp Ala Ala Leu Arg Thr Met Ile Pro Phe Arg Pro Lys Pro Arg Phe
 65                  70                  75                  80

Pro Ala Pro Gln Pro Leu Gly Leu Phe Ser Tyr Leu Thr Val Ser Trp
                 85                  90                  95

Leu Thr Pro Leu Met Ile Gln Ser Leu Arg Ser Arg Leu Asp Glu Asn
             100                 105                 110
```

```
Thr Ile Pro Pro Leu Ser Val His Asp Ala Ser Asp Lys Asn Val Gln
        115                 120                 125

Arg Leu His Arg Leu Trp Glu Glu Val Ser Arg Arg Gly Ile Glu
130                 135                 140

Lys Ala Ser Val Leu Leu Val Met Leu Arg Phe Gln Arg Thr Arg Leu
145                 150                 155                 160

Ile Phe Asp Ala Leu Leu Gly Ile Cys Phe Cys Ile Ala Ser Val Leu
                165                 170                 175

Gly Pro Ile Leu Ile Pro Lys Ile Leu Glu Tyr Ser Glu Glu Gln
                180                 185                 190

Leu Gly Asn Val Val His Gly Val Gly Leu Cys Phe Ala Leu Phe Leu
        195                 200                 205

Ser Glu Cys Val Lys Ser Leu Ser Phe Ser Ser Trp Ile Ile Asn
        210                 215                 220

Gln Arg Thr Ala Ile Arg Phe Gln Ala Val Ser Ser Phe Ala Phe
225                 230                 235                 240

Glu Lys Leu Ile Gln Phe Lys Ser Val Ile His Ile Thr Ser Gly Glu
                245                 250                 255

Ala Ile Ser Phe Phe Thr Gly Asp Val Asn Tyr Leu Phe Glu Gly Val
                260                 265                 270

Cys Tyr Gly Pro Leu Val Leu Ile Thr Cys Ala Ser Leu Val Ile Cys
        275                 280                 285

Ser Ile Ser Ser Tyr Phe Ile Ile Gly Tyr Thr Ala Phe Ile Ala Ile
        290                 295                 300

Leu Cys Tyr Leu Leu Val Phe Pro Leu Glu Val Phe Met Thr Arg Met
305                 310                 315                 320

Ala Val Lys Ala Gln His His Thr Ser Glu Val Ser Asp Gln Arg Ile
                325                 330                 335

Arg Val Thr Ser Glu Val Leu Thr Cys Ile Lys Leu Ile Lys Met Tyr
                340                 345                 350

Thr Trp Glu Lys Pro Phe Ala Lys Ile Ile Glu Asp Leu Arg Arg Lys
                355                 360                 365

Glu Arg Lys Leu Leu Glu Lys Cys Gly Leu Val Gln Ser Leu Thr Ser
                370                 375                 380

Ile Thr Leu Phe Ile Ile Pro Thr Val Ala Thr Ala Val Trp Val Leu
385                 390                 395                 400

Ile His Thr Ser Leu Lys Leu Lys Leu Thr Ala Ser Met Ala Phe Ser
                405                 410                 415

Met Leu Ala Ser Leu Asn Leu Leu Arg Leu Ser Val Phe Phe Val Pro
                420                 425                 430

Ile Ala Val Lys Gly Leu Thr Asn Ser Lys Ser Ala Val Met Arg Phe
                435                 440                 445

Lys Lys Phe Phe Leu Gln Glu Ser Pro Val Phe Tyr Val Gln Thr Leu
                450                 455                 460

Gln Asp Pro Ser Lys Ala Leu Val Phe Glu Glu Ala Thr Leu Ser Trp
465                 470                 475                 480

Gln Gln Thr Cys Pro Gly Ile Val Asn Gly Ala Leu Glu Leu Glu Arg
                485                 490                 495

Asn Gly His Ala Ser Glu Gly Met Thr Arg Pro Arg Asp Ala Leu Gly
                500                 505                 510

Pro Glu Glu Glu Gly Asn Ser Leu Gly Pro Glu Leu His Lys Ile Asn
                515                 520                 525
```

```
Leu Val Val Ser Lys Gly Met Met Leu Gly Val Cys Gly Asn Thr Gly
        530                 535                 540

Ser Gly Lys Ser Ser Leu Leu Ser Ala Ile Leu Glu Glu Met His Leu
545                 550                 555                 560

Leu Glu Gly Ser Val Gly Val Gln Gly Ser Leu Ala Tyr Val Pro Gln
                565                 570                 575

Gln Ala Trp Ile Val Ser Gly Asn Ile Arg Glu Asn Ile Leu Met Gly
            580                 585                 590

Gly Ala Tyr Asp Lys Ala Arg Tyr Leu Gln Val Leu His Cys Cys Ser
        595                 600                 605

Leu Asn Arg Asp Leu Glu Leu Leu Pro Phe Gly Asp Met Thr Glu Ile
    610                 615                 620

Gly Glu Arg Gly Leu Asn Leu Ser Gly Gly Gln Lys Gln Arg Ile Ser
625                 630                 635                 640

Leu Ala Arg Ala Val Tyr Ser Asp Arg Gln Ile Tyr Leu Leu Asp Asp
                645                 650                 655

Pro Leu Ser Ala Val Asp Ala His Val Gly Lys His Ile Phe Glu Glu
            660                 665                 670

Cys Ile Lys Lys Thr Leu Arg Gly Lys Thr Val Leu Val Thr His
        675                 680                 685

Gln Leu Gln Tyr Leu Glu Phe Cys Gly Gln Ile Ile Leu Leu Glu Asn
    690                 695                 700

Gly Lys Ile Cys Glu Asn Gly Thr His Ser Glu Leu Met Gln Lys Lys
705                 710                 715                 720

Gly Lys Tyr Ala Gln Leu Ile Gln Lys Met His Lys Glu Ala Thr Ser
                725                 730                 735

Val Phe Arg Cys Pro Met Ser Phe Phe Asp Thr Ile Pro Ile Gly Arg
            740                 745                 750

Leu Leu Asn Cys Phe Ala Gly Asp Leu Glu Gln Leu Asp Gln Leu Leu
        755                 760                 765

Pro Ile Phe Ser Glu Gln Phe Leu Val Leu Ser Leu Met Val Ile Ala
    770                 775                 780

Val Leu Leu Ile Val Ser Val Leu Ser Pro Tyr Ile Leu Leu Met Gly
785                 790                 795                 800

Ala Ile Ile Met Val Ile Cys Phe Ile Tyr Tyr Met Met Phe Lys Lys
                805                 810                 815

Ala Ile Gly Val Phe Lys Arg Leu Glu Asn Tyr Ser Arg Ser Pro Leu
            820                 825                 830

Phe Ser His Ile Leu Asn Ser Leu Gln Gly Leu Ser Ser Ile His Val
        835                 840                 845

Tyr Gly Lys Thr Glu Asp Phe Ile Ser Gln Phe Lys Arg Leu Thr Asp
    850                 855                 860

Ala Gln Asn Asn Tyr Leu Leu Leu Phe Leu Ser Ser Thr Arg Trp Met
865                 870                 875                 880

Ala Leu Arg Leu Glu Ile Met Thr Asn Leu Val Thr Leu Ala Val Ala
                885                 890                 895

Leu Phe Val Ala Phe Gly Ile Ser Ser Thr Pro Tyr Ser Phe Lys Val
            900                 905                 910

Met Ala Val Asn Ile Val Leu Gln Leu Ala Ser Ser Phe Gln Ala Thr
        915                 920                 925

Ala Arg Ile Gly Leu Glu Thr Glu Ala Gln Phe Thr Ala Val Glu Arg
    930                 935                 940

Ile Leu Gln Tyr Met Lys Met Cys Val Ser Glu Ala Pro Leu His Met
```

```
                945            950           955            960
            Glu Gly Thr Ser Cys Pro Gln Gly Trp Pro Gln His Gly Glu Ile Ile
                       965                 970                 975
            Phe Gln Asp Tyr His Met Lys Tyr Arg Asp Asn Thr Pro Thr Val Leu
                       980                 985                 990
            His Gly Ile Asn Leu Thr Ile Arg Gly His Glu Val Val Gly Ile Val
                       995                1000                1005
            Gly Arg Thr Gly Ser Gly Lys Ser Ser Leu Gly Met Ala Leu Phe Arg
                      1010                1015                1020
            Leu Val Glu Pro Met Ala Gly Arg Ile Leu Ile Asp Gly Val Asp Ile
            1025                1030                1035                1040
            Cys Ser Ile Gly Leu Glu Asp Leu Arg Ser Lys Leu Ser Val Ile Pro
                      1045                1050                1055
            Gln Asp Pro Val Leu Leu Ser Gly Thr Ile Arg Phe Asn Leu Asp Pro
                      1060                1065                1070
            Phe Asp Arg His Thr Asp Gln Gln Ile Trp Asp Ala Leu Glu Arg Thr
                      1075                1080                1085
            Phe Leu Thr Lys Ala Ile Ser Lys Phe Pro Lys Lys Leu His Thr Asp
                      1090                1095                1100
            Val Val Glu Asn Gly Gly Asn Phe Ser Val Gly Glu Arg Gln Leu Leu
            1105                1110                1115                1120
            Cys Ile Ala Arg Ala Val Leu Arg Asn Ser Lys Ile Leu Ile Leu Asp
                      1125                1130                1135
            Glu Ala Thr Ala Ser Ile Asp Met Glu Thr Asp Thr Leu Ile Gln Arg
                      1140                1145                1150
            Thr Ile Arg Glu Ala Phe Gln Gly Cys Thr Val Leu Val Ile Ala His
                      1155                1160                1165
            Arg Val Thr Thr Val Leu Asn Cys Asp His Ile Leu Val Met Gly Asn
                      1170                1175                1180
            Gly Lys Val Val Glu Phe Asp Arg Pro Glu Val Leu Arg Lys Lys Pro
            1185                1190                1195                1200
            Gly Ser Leu Phe Ala Ala Leu Met Ala Thr Ala Thr Ser Ser Leu Arg
                      1205                1210                1215

<210> SEQ ID NO 25
<211> LENGTH: 5020
<212> TYPE: DNA
<213> ORGANISM: homo sapiens

<400> SEQUENCE: 25
agagacagga acagagcccc tcatctcacc tctgggctac catacagaaa agcaggtgta      60
tttgaataaa ccaggttggc aaatcatact atagctgaaa gaattggcag gaactgaaaa     120
tgactaggaa gaggacatac tgggtgccca actcttctgg tggcctcgtg aatcgtggca     180
tcgacatagg cgatgacatg gtttcaggac ttatttataa aacctatact ctccaagatg     240
gcccctggag tcagcaagag agaaatcctg aggctccagg gagggcagct gtcccaccgt     300
gggggaagta tgatgctgcc ttgagaacca tgattccctt ccgtcccaag ccgaggtttc     360 ctgccccca gcccctggac aatgctggcc tgttctccta cctcaccgtg tcatggctca     420
ccccgctcat gatccaaagc ttacggagtc gcttagatga aacaccatc cctccactgt     480 cagtccatga tgcctcagac aaaaatgtcc aaaggcttca ccgcctttgg gaagaagaag     540
tctcaaggcg agggattgaa aaagcttcag tgcttctggt gatgctgagg ttccagagaa     600
caaggttgat tttcgatgca cttctgggca tctgcttctg cattgccagt gtactcgggc     660
```

-continued

```
cagactgcac caatgggga ggtgggagtc ttcccagaag aaaactgagg cactggtacc    720
agctacgggg aggtgaagat attgattata ccaaagatcc tggaatattc agaagagcag    780
ttggggaatg ttgtccatgg agtgggactc tgctttgccc ttttcctctc cgaatgtgtg    840
aagtctctga gtttctcctc cagttggatc atcaaccaac gcacagccat caggttccaa    900
gcagctgttt cctcctttgc ctttgagaag ctcatccaat ttaagtctgt aatacacatc    960
acctcaggag aggccatcag cttcttcacc ggtgatgtaa actacctgtt tgaagggggtg   1020
tgctatggac ccctagtact gatcacctgc gcatcgctgg tcatctgcag catttcttcc   1080
tacttcatta ttggatacac tgcatttatt gccatcttat gctatctcct ggttttccca   1140
ctggaggtat tcatgacaag aatggctgtg aaggctcagc atcacacatc tgaggtcagc   1200
gaccagcgca tccgtgtgac cagtgaagtt ctcacttgca ttaagctgat taaaatgtac   1260
acatgggaga aaccatttgc aaaaatcatt gaagacctaa gaaggaagga aaggaagcta   1320
ttggagaagt gcgggcttgt ccagagcctg acaagtataa ccttgttcat catccccaca   1380
gtggccacag cggtctgggt tctcatccac acatccttaa agctgaaact cacagcgtca   1440
atggccttca gcatgctggc ctccttgaat ctccttcggc tgtcagtgtt ctttgtgcct   1500
attgcagtca aaggtctcac gaattccaag tctgcagtga tgaggttcaa gaagtttttc   1560
ctccaggaga gccctgtttt ctatgtccag acattacaag accccagcaa agctctggtc   1620
tttgaggagg ccaccttgtc atggcaacag acctgtcccg ggatcgtcaa tgggcactg   1680
gagctggaga ggaacgggca tgcttctgag gggatgacca ggcctagaga tgccctcggg   1740
ccagaggaag aagggaacag cctgggccca gagttgcaca agatcaacct ggtggtgtcc   1800
aagggggatga tgttaggggt ctgcggcaac acggggagtg gtaagagcag cctgttgtca   1860
gccatcctgg aggagatgca cttgctcgag ggctcggtgg gggtgcaggg aagcctggcc   1920
tatgtcccc agcaggcctg gatcgtcagc gggaacatca gggagaacat cctcatggga   1980
ggcgcatatg acaaggcccg atacctccag gtgctccact gctgctccct gaatcgggac   2040
ctggaacttc tgcccttggg agacatgaca gagattggag agcggggcct caacctctct   2100
ggggggcaga acagaggat cagcctggcc cgcgccgtct attccgaccg tcagatctac   2160
ctgctgacg accccctgtc tgctgtggac gcccacgtgg ggaagcacat ttttgaggag   2220
tgcattaaga gacactcag ggggaagacg gtcgtcctgg tgacccacca gctgcagtac   2280
ttagaatttt gtggccagat catttgttg gaaaatggga aaatctgtga aaatggaact   2340
cacagtgagt taatgcagaa aaaggggaaa tatgcccaac ttatccagaa gatgcacaag   2400
gaagccactt cggacatgtt gcaggacaca gcaaagatag cagagaagcc aaaggtagaa   2460
agtcaggctc tggccacctc cctggaagag tctctcaacg gaaatgctgt gccggagcat   2520
cagctcacac aggaggagga gatggaagaa ggctccttga gttggagggt ctaccaccac   2580
tacatccagg cagctggagg ttacatggtc tcttgcataa ttttcttctt cgtggtgctg   2640
atcgtcttct taacgatctt cagcttctgg tggctgagct actggttgga gcagggctcg   2700
ggaccaata gcagccgaga gagcaatgga accatggcag acctgggcaa cattgcagac   2760
aatcctcaac tgtccttcta ccagctggtg tacgggctca acgccctgct cctcatctgt   2820
gtgggggtct gctcctcagg gattttcacc aaggtcacga ggaaggcatc cacggccctg   2880
cacaacaagc tcttcaacaa ggttttccgc tgccccatga gtttctttga caccatccca   2940
ataggccggc ttttgaactg cttcgcaggg gacttggaac agctgaccca gctcttgccc   3000
```

-continued

```
atcttttcag agcagttcct ggtcctgtcc ttaatggtga tcgccgtcct gttgattgtc    3060
agtgtgctgt ctccatatat cctgttaatg ggagccataa tcatggttat ttgcttcatt    3120
tattatatgt gagtaggttc tttttgcttg tgacttgggg agcaagggct gggaccaacc    3180
cagactagat ggtcccagag gtggacggtc caggtccctt acctccactg tccatgcagg    3240
atgttcaaga aggccatcgg tgtgttcaag agactggaga actatagccg gtctccttta    3300
ttctcccaca tcctcaattc tctgcaaggc ctgagctcca tccatgtcta tggaaaaact    3360
gaagacttca tcagccagtg agtccttctg ctgccatttt gagaatgatg gaaccaccag    3420
gggtgggtgg ggagccaggg aaagaatggg acgtcttgag agtggatcat cttcaaaaag    3480
cattcagaga gccacattgg tcgattgaga cgtattctct gagccttcca gaacctgctg    3540
gaaccattct ttcatttaag aggctgactg atgcgcagaa taactacctg ctgttgtttc    3600
tatcttccac acgatggatg gcattgaggc tggagatcat gaccaacctt gtgaccttgg    3660
ctgttgccct gttcgtggct tttggcattt cctccacccc ctactccttt aaagtcatgg    3720
ctgtcaacat cgtgctgcag ctggcgtcca gcttccaggc cactgcccgg attggcttgg    3780
agacagaggc acagttcacg gctgtagaga ggatactgca gtacatgaag atgtgtgtct    3840
cggaagctcc tttacacatg gaaggcacaa gttgtcccca ggggtggcca cagcatgggg    3900
aaatcatatt tcaggattat cacatgaaat acagagacaa cacacccacc gtgcttcacg    3960
gcatcaacct gaccatccgc ggccacgaag tggtgggcat cgtgggaagg acgggctctg    4020
ggaagtcctc cttgggcatg gctctcttcc gcctggtgga gcccatggca ggccggattc    4080
tcattgacgg cgtggacatt tgcagcatcg gcctggagga cttgcggtcc aagctctcag    4140
tgatccctca agatccagtg ctgctctcag gaaccatcag attcaaccta gatcccttg     4200
accgtcacac tgaccagcag atctgggatg ccttggagag gacattcctg accaaggcca    4260
tctcaaagtt ccccaaaaag ctgcatacag atgtggtgga aaacggtgga aacttctctg    4320
tgggggagag gcagctgctc tgcattgcca gggctgtgct tcgcaactcc aagatcatcc    4380
ttatcgatga agccacagcc tccattgaca tggagacaga caccctgatc cagcgcacaa    4440
tccgtgaagc cttccagggc tgcaccgtgc tcgtcattgc ccaccgtgtc accactgtgc    4500
tgaactgtga ccacatcctg gttatgggca atgggaaggt ggtagaattt gatcggccgg    4560
aggtactgcg gaagaagcct gggtcattgt tcgcagccct catggccaca gccacttctt    4620
cactgagata aggagatgtg gagacttcat ggaggctggc agctgagctc agaggttcac    4680
acaggtgcag cttcgaggcc cacagtctgc gaccttcttg tttggagatg agaacttctc    4740
ctggaagcag gggtaaatgt agggggggtg gggattgctg gatggaaacc ctggaatagg    4800
ctacttgatg gctctcaaga ccttagaacc ccagaaccat ctaagacatg ggattcagtg    4860
atcatgtggt tctccttta acttacatgc tgaataattt tataataagg taaaagctta    4920
tagttttctg atctgtgtta gaagtgttgc aaatgctgta ctgactttgt aaaatataaa    4980
actaaggaaa actcaaaaaa aaaaaaaaa aaaaaaaaa                            5020
```

POLYNUCLEOTIDES ENCODING HUMAN TRANSPORTER PROTEINS

The present application claims the benefit of U.S. Provisional Application No. 60/163,018 which was filed on Nov. 2, 1999 and is herein incorporated by reference in its entirety.

1. INTRODUCTION

The present invention relates to the discovery, identification, and characterization of novel human polynucleotides encoding proteins that share sequence similarity with mammalian transporter proteins. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed genes that can be used for diagnosis, drug screening, clinical trial monitoring, the treatment of diseases and disorders, or otherwise contributing to the quality of life.

2. BACKGROUND OF THE INVENTION

Transporter proteins are integral membrane proteins that mediate or facilitate the passage of materials across the lipid bilayer. Given that the transport of materials across the membrane can play an important physiological role, transporter proteins are good drug targets. Additionally, one of the mechanisms of drug resistance involves diseased cells using cellular transporter systems to export chemotherapeutic agents from the cell. Such mechanisms are particularly relevant to cells manifesting resistance to a multiplicity of drugs.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with mammalian multi-drug resistance (MDR) proteins and cellular transporters.

The novel human nucleic acid sequences described herein, encode alternative proteins/open reading frames (ORFs) of 659, 705, 1,063, 496, 542, 900, 978, 1,024, 1,382, 815, 861, 1,219, and amino acids in length (see SEQ ID NOS: 2, 4, 6, 8, 10, 12, 14, 16, 18, 20, 22, and 24 respectively).

The invention also encompasses agonists and antagonists of the described NHPs, including small molecules, large molecules, mutant NHPs, or portions thereof that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP genes (e.g., expression constructs that place the described gene under the control of a strong promoter system), and transgenic animals that express a NHP transgene, or "knockouts" (which can be conditional) that do not express a functional NHP. A knockout ES cell line has been produced that contains a gene trap mutation in the murine ortholog of the described gene.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the described NHP ORFs that encode the described NHP amino acid sequences. SEQ ID NO:25 describes a NHP ORF as well as flanking 5' and 3' sequences.

5. DETAILED DESCRIPTION OF THE INVENTION

The NHPs, described for the first time herein, are novel proteins that are expressed in, inter alia, human cell lines, predominantly in human mammary gland, as well as human fetal liver, prostate, testis, and gene trapped human cells.

The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products;

(b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence in deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 680° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP gene nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. The oligonucleotides, typically between about 16 to about 40 (or any whole number within the stated range) nucleotides in length can partially overlap each other and/or the NHP sequence may be represented using oligonucleotides that do not overlap. Accordingly, the described NHP polynucleotide sequences shall typically comprise at least about two or three distinct oligonucleotide sequences of at least about 18, and preferably about 25, nucleotides in length that are each first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the human cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding the NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHPs are presented in the Sequence Listing. The NHP nucleotides were obtained from clustered human gene trapped sequences, ESTs, and human testis and mammary gland cDNA libraries (Edge Biosystems, Gaithersburg, Md.). The described sequences can also incorporate several coding region single nucleotide polymorphisms (cSNPs). The first polymorphism is a A to G transition at position 704 of, for example, SED ID NO: 23, which results in a corresponding change of gln to an arg at, for example, position 235 of SEQ ID NO:24; the second can occur at position 2184 of, for example, SEQ ID NO:23 that changes a gln to a his at position 728 of, for example, SEQ ID NO:24; and the third cSNP involves a silent T to C transition at position 2,436 of, for example, SEQ ID NO:23.

Similar MDR encoding sequences, uses, and applications that are germane to the described NHPs, are described in U.S. Pat. Nos. 5,198,344 and 5,866,699 which are herein incorporated by reference in their entirety.

5.2 NHPS and NHP Polypeptides

NHPs, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, for the identification of other cellular gene products related to a NHP, as reagents in assays for screening for compounds that can be as pharmaceutical reagents useful in the therapeutic treatment of mental, biological, or medical disorders and diseases. Given the similarity information and expression data, the described NHPs can be targeted (by drugs, oligos, antibodies, etc,) in order to treat disease, or to therapeutically augment the efficacy of, for example, chemotherapeutic agents used in the treatment of breast or prostate cancer.

The Sequence Listing discloses the amino acid sequences encoded by the described NHP genes. The NHPs typically display have initiator methionines in DNA sequence contexts consistent with a translation initiation site.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., E. coli, B. subtilis) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited to, the E. coli expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhidrosis virus (AcNPV) is used as a vector to express foreign genes. The virus grows in Spodoptera frugiperda cells. A NHP gene coding sequence may be cloned individually into non-essential regions (for example the polyhedrin gene) of the virus and placed under control of an AcNPV promoter (for example the polyhedrin promoter). Successful insertion of NHP gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$. nitriloacetic acid-agarose columns and histidine-tagged proteins are selectively eluted with imidazole-containing buffers.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding the a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (*bacille Calmette-Guerin*) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:
1. An isolated nucleic acid molecule comprising the nucleotide sequence of SEQ ID NO:23.
2. An isolated nucleic acid molecule comprising a nucleotide sequence that encodes the amino acid sequence of SEQ ID NO:24.
3. An expression vector comprising a nucleic acid sequence encoding the amino acid sequence of SEQ ID NO: 24.
4. A cell comprising the expression vector of claim 3.

* * * * *